United States Patent [19]

Gowravaram et al.

[11] Patent Number: 5,618,844
[45] Date of Patent: Apr. 8, 1997

[54] HYDROXAMIC ACID AND CARBOXYLIC ACID DERIVATIVES, PROCESS FOR THEIR PREPARATION AND USE THEREOF

[75] Inventors: Madhusudhan R. Gowravaram, West Chester; Jeffrey Johnson, Phoenixville; Ewell R. Cook, Royersford; Robert C. Wahl, Collegeville; Alan M. Mathiowetz, Schwenksville; Bruce E. Tomczuk, Collegeville; Ashis K. Saha, Harleysville, all of Pa.

[73] Assignee: Sanofi S.A., Paris Cedex, France

[21] Appl. No.: 461,079

[22] Filed: Jun. 5, 1995

Related U.S. Application Data

[62] Division of Ser. No. 201,837, Feb. 25, 1994, Pat. No. 5,514,716.

[51] Int. Cl.⁶ .......................... A61K 31/19; C07C 239/00
[52] U.S. Cl. .......................................... 514/575; 562/621
[58] Field of Search ........................... 562/800, 621; 514/575, 419; 548/490

[56] References Cited

PUBLICATIONS

Blodgett, et al., J. Am. Chem. Soc. 107(14), 4305–13.

*Primary Examiner*—Joseph Conrad
*Attorney, Agent, or Firm*—William J. Davis; Paul E. Dupont

[57] ABSTRACT

This disclosure relates to a novel class of hydroxamic and carboxylic acid based matrix metalloproteinase inhibitor derivatives. The disclosure further relates to pharmaceutical compositions containing such compounds and to the use of such compounds and compositions in the treatment of matrix metalloproteinase induced diseases.

15 Claims, No Drawings

HYDROXAMIC ACID AND CARBOXYLIC ACID DERIVATIVES, PROCESS FOR THEIR PREPARATION AND USE THEREOF

This application is division of application Ser. No. 08/201,837 filed Feb. 25, 1994 now U.S. Pat. No. 5,514,716.

FIELD OF THE INVENTION

The invention is directed to pharmaceuticals useful in diseases characterized by unwanted matrix metalloproteinase activity.

BACKGROUND OF THE INVENTION

A number of small peptide like compounds which inhibit metalloproteinase have been described. Perhaps the most notable of these are those relating to the angiotension converting enzyme (ACE) where such agents act to blockade the conversion of the decapeptide angiotension I to angiotension II, a potent pressor substance. Compounds of this type are described in EP-A-0012401.

Certain hydroxamic acids have been suggested as collagenase inhibitor as in U.S. Pat. No. 4,599,361; WO-A-9005716 and WO-A-9005719. Other hydroxamic acids have been prepared as ACE inhibitors, for example, in U.S. Pat. No. 4,105,789, while still others have been described as enkephalinase inhibitors as in U.S. Pat. No. 4,495,540.

The hydroxamic and carboxylic acids of the current invention act as inhibitors of mammalian matrix metalloproteinases (MMPs). The MMPs include, for example, collagenase, stromelysin and gelatinase. Since the MMPs are involved in the breakdown of the extracellular matrix of articular cartilage (*Arthritis and Rheumatism,* 20, 1231–1239, (1977)), potent inhibitors of the MMPs may be useful in the treatment of arthritides, for example, osteoarthritis and rheumatoid arthritis and other diseases which involve the breakdown of extracellular matrix. These diseases include corneal ulceration, osteoporosis, periodontitis, tumor growth and metastasis.

The use of hydroxamic acid derivatives for the effective inhibition of the destruction of articular cartilage as a model of rheumatoid and osteoarthritis has been demonstrated (Int. J. Tiss. Reac., XIII, 237–243 (1991)).

Topical application of hydroxamate inhibitors may be effective against corneal ulceration as demonstrated in the alkali-injured cornea model (Invest. Ophthalmol Vis. Sci., 33, 33256–3331 (1991)).

In periodontitis, the effecticeness of tetracycline has been attributed to its collagenase inhibitory activaty (J. Perio. Res., 28, 379–385 (1993)).

Hydroxamic acid derivatives have also been effective in models of tumor growth (Cancer Research, 53, 2087–2091 (1993) and tumor invasion (Mol. Cell Biol., 9, 2133–2141 (1989)).

The current invention relates to a series of hydroxamic and carboxylic acids, which act as inhibitors of matrix metalloproteinases, their preparation, pharmaceutical compositions containing them, and the intermediates involved in their preparation.

SUMMARY OF THE INVENTION

This invention provides compounds which are matrix metalloproteinase inhibitors. The compounds have the structure:

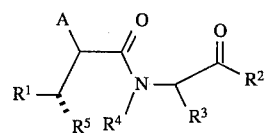

wherein

A is $A^1-A^2-A^3$ $A^1$ is $C_{1-10}$ alkyl, $C_{2-10}$ alkene, $C_{2-10}$ alkyne having $C_{1-5}$ in the backbone or a chemical bond;

$A^2$ is X–Y–Z; wherein
  X is a chemical bond, —O—, —NH—, or —S—;
  Y is —CO—, or —CHR$^9$—; and
  Z is —O—, —NH—, —S—, or a chemical bond;

$A^3$ is hydrogen, $C_{1-6}$ alkyl, substituted $C_{1-6}$ alkyl, aryl, substituted aryl, heteroaryl, substituted heteroaryl, heterocyclic, substituted heterocyclic, aryl $C_{1-6}$ alkyl, heteroaryl $C_{1-6}$ alkyl, substituted heteroaryl $C_{1-6}$ alkyl, or substituted heterocyclic $C_{1-6}$ alkyl;

with the proviso that
  (a) at least one X, Y and Z must contain a heteroatom;
  (b) when Y is —CH$_2$—, then only one of X and Z can be a heteroatom;
  (c) when Y is —CO— and both X and Z are heteroatoms, then one must be —NH— and the other —NH— or —O—;
  (d) when $A^1$ is alkyl, X is —O— or —S—, Y is CHR$^9$ and Z is a chemical bond, then $A^3$ cannot be H or $C_{1-6}$ alkyl;
  (e) when $A^1$ is alkyl, X is a chemical bond, Y is CHR$^9$ and Z is —O— or —S—, then $A^3$ cannot be $C_{1-6}$ alkyl;
  (f) when $A^1$ is a chemical bond, X is O or S, Y is CH$_2$, and Z is a chemical bond, then $A^3$ cannot be aryl or aryl $C_{1-6}$ alkyl;
  (g) when $A^1$ is a chemical bond, X is a chemical bond, Y is CO, and Z is O, then $A^3$ cannot be H, alkyl, aryl, aryloxyalkyl, alkanoyloxyalkyl or aroyloxyalkyl; or
  (h) when $A^1$ is a chemical bond, X is a NH, Y is CH$_2$, and Z is a chemical bond, then $A^3$ cannot be alkyl, aryl, arylalkyl, cycloalkyl, or cycloalkyl alkyl;

$R^1$ is HN(OH)CO—, HCON(OH)—, CH$_3$CON(OH)—, HO$_2$C—, HS—, or phosphinate;

$R^2$ is OR$^6$ or NR$^{10}$R$^6$
  where R$^6$ is hydrogen, C$_{6-12}$ aryl, or (CH$_2$)$_n$R$^7$,
    wherein R$^7$ is hydrogen phenyl, substituted phenyl, hydroxy, C$_{1-6}$ alkoxy, C$_{2-7}$ acyloxy, C$_{1-6}$ alkylthio, phenylthio, sulfoxide of a thio, sulfone of a thio, carboxyl, (C$_{1-6}$ alkyl) carbonyl, (C$_{1-6}$ alkoxy) carbonyl, (C$_{1-6}$ alkyl)aminocarbonyl, arylaminocarbonyl, amino, substituted acyclic amino, heterocyclic amino, N-oxide of an amine, or C$_{2-7}$ acylamino, and n is 1 to 6; or R$^3$ and R$^6$ taken together are a group of the formula
  —(CH$_2$)$_m$—
  where m is from 5 to 12, optionally interrupted by a NR$^8$ group
    where R$^8$ is selected from hydrogen, C$_{1-6}$ alkyl, C$_{1-6}$ alkylcarbonyl, in each of which the aryl moiety is optionally substituted;

R$^3$ is a characterizing group of an alpha amino acid, C$_{1-6}$ alkyl, aryl methylene, substituted aryl methylene, C$_{3-10}$ cycloalkyl, C$_{3-10}$ cycloalkyl methylene, aryl, substituted aryl, fused bicycloaryl methylene, fused substituted bicycloaryl methylene, conjugated bicycloaryl methylene, or conjugated substituted bicycloaryl methylene;

$R^4$ is hydrogen or $C_{1-4}$ alkyl;

$R^5$ is hydrogen, phenyl, substituted phenyl, amino, hydroxy, mercapto, $C_{1-4}$ alkoxy, $C_{1-6}$ alkylamino, $C_{1-6}$ alkylthio, $C_{1-6}$ alkyl or $C_{2-6}$ alkenyl,
optionally substituted by
alkyl, phenyl, substituted phenyl, heterocylic, substituted heterocylic, amino, acylated amino, protected amino, hydroxy, protected hydroxy, mercapto, protected mercapto, carboxy, protected carboxy, or amidated carboxy;

$R^9$ is hydrogen or $C_{1-4}$ alkyl;

$R^{10}$ is hydrogen or $C_{1-4}$ alkyl;

and the salts, solvates and hydrates thereof.

Preferred compounds have the structure:

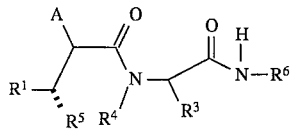

wherein
A is $A^1-A^2-A^3$
wherein
$A^1$ is $(CH_2)_n$, and n is 3–5,
$A^2$ is X–Y–Z,
wherein,
X is a chemical bond or —NH—;
Y is —(C=O)—, —$CH_2$—, —(CHCH$_3$)—,
Z is —O—, —NH—, or a chemical bond; and
$A^3$ is
hydrogen, methyl, ethyl, propyl, butyl, pentyl, phenyl, methylphenyl, chlorophenyl, methoxyphenyl, phenylmethylene, methoxyphenylmethylene, methylphenylmethylene or phenylethylene;

$R^1$ is $HO_2C$— or HN(OH);

$R^3$ is
tertiary butyl, phenylmethylene, cyclohexyl methylene, or 3,5 dimethyl phenylmethylene;

$R^4$ is hydrogen or methyl;

$R^5$ is hydrogen, methyl, 2-methylpropyl, or 1,3-dihydro-1,3-dioxo-2H-isoindol-2-yl; and $R^6$ is
methyl,
2-pyridylethylene,
phenylethylene,
4-sulfamoyl phenylethylene, or
morpholino-N-ethylene;

Even more preferred are compounds wherein A is
—$(CH_2)_4$—O—H,
—$(CH_2)_3$—C=O—O—H,
—$(CH_2)_3$—C=O—NH—$(CH_2)_2CH_3$,
—$(CH_2)_3$—C=O—NH—$(CH_2)_2$-phenyl
—$(CH_2)_3$—CH($CH_3$)—O—H,
—$(CH_2)_4$—NH—C=O—$(CH_2)_2CH_3$,
—$(CH_2)_4$—O—phenyl,
—$(CH_2)_4$—O—(4-chlorophenyl),
—$(CH_2)_4$—O—(3-methylphenyl),
—$(CH_2)_4$—O—(4-methoxyphenyl),
—$(CH_2)_4$—O—(4-methylphenyl),
—$(CH_2(_5)$—)—phenyl,
—$(CH_2)_4$—O—$CH_2$-phenyl
—$(CH_2)_5$—O—$CH_2$—(4-methylphenyl), or
—$(CH_2)_3$—O—$CH_2$—(4-methylphenyl).

Included in the invention are pharmaceutical compositions comprising an effective amount of at least one of the compounds and methods of promoting an antiarthritic effect in a mammal in need thereof comprising administering thereto a matrix metalloproteinase inhibitory effective amount of at least one compound of the invention.

DETAILED DESCRIPTION OF THE INVENTION

Hereafter in this specification the term "compound" includes salt solvates and hydrates unless the context requires otherwise.

As used herein the term "$C_{1-6}$ alkyl" refers to a straight or branched chain alkyl moiety having from one to six carbon atoms, including for example, methyl, ethyl, propyl, isopropyl, butyl, t-butyl, pentyl, hexyl and the like.

The term "$C_{2-6}$ alkenyl" refers to a straight or branched chain alkyl moiety having two to six carbons and having in addition one double bond, of either E or Z stereochemistry where applicable. This term would include, for example, vinyl, 1-propenyl, 1- and 2-butenyl, 2-methyl-2-propenyl etc.

The term "cycloalkyl" refers to a saturated alicyclic moiety having from 3 to 8 carbon atoms and includes for example, cyclopropyl, cyclobutyl, cyclopentyl, cyclohexyl and the like.

The term "heterocyclic" refers to a saturated or unsaturated ring containing at least one hetero atom such as nitrogen, oxygen or sulphur and includes for example, furan, pyrrole, thiophen, morpholine, pyridine, dioxane, imidazoline, pyrimidine, pyridazine and the like.

The term "substituted", as applied to a phenyl or other aromatic ring, means substituted with up to four substituents each of which independently may be $C_{1-6}$ alkyl, $C_{1-6}$ alkoxy, hydroxy, thiol, $C_{1-6}$ alkylthiol, amino, substituted amino, halo (including fluoro, chloro, bromo and iodo), trifluoromethyl, nitro, —COOH, —$CONH_2$ or —$CONHR^A$, wherein $R^A$ represents a $C_{1-6}$ alkyl group or an amino acid such as alanine, valine, leucine, isoleucine, phenylalanine, tryptophan, methionine, glycine, serine, threonine, cysteine, tyrosine, asparagine, glutamine, aspartic acid, glutamic acid, lysine, arginine or histidine.

The term "amino acid" means one of the following R or S alpha-amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

Derivatives of amino acids include acid halides, esters and substituted or unsubstituted amides, for example N-methyl amide.

There are several chiral centers in the compounds according to the invention because of the presence of asymmetric carbon atoms.

The presence of several asymmetric carbon atoms gives rise to a number of diastereomers with the appropriate R or S stereochemistry at each chiral center. The invention is understood to include all such diastereomers and mixtures thereof.

Preferred compounds include the following:
a) N-[(2R)-2-[2'-(Hydroxyamino)-2'-(oxo)ethyl]-5-(carboxy)pentanoyl]-L-phenylalanine N-methylamide;

b) N-[(2R)-2-[2'-(Hydroxyamino)-2'-(oxo)ethyl]-6-(phenylmethoxy)hexanoyl]-L-phenylalanine N-methylamide;

c) N-[(2R)-2-[2'-(Hydroxyamino)-2'-(oxo)ethyl]-6-(propylamino)-6-(oxo)hexanoyl]-L-phenylalanine N-methylamide;

d) N-[(2R)-2-[2'-(Hydroxyamino)-2'-(oxo)ethyl]-(6RS)-6-(hydroxy)heptanoyl]-L-phenylalanine N-methylamide;

e) (2S)-N-2-[(2'R)-2'-[2"-(Hydroxyamino)-2"-(oxo)ethyl]-6'-(hydroxy)hexanoyl]amino-3,3-dimethylbutanoic acid N-methylamide;

f) (2S)-N-2-[(2'R)-2'-[2"-(Hydroxyamino)-2"-(oxo)ethyl]-6'-(phenylmethoxy)hexanoyl]amino-3,3-dimethylbutanoic acid N-methylamide;

g) N-[(2'R)-2-[2'-(Hydroxyamino)-2'-(oxo)ethyl]-6-(4'-oxobutylamino)hexanoyl]-L-phenylalanine N-methylamide;

h) 2(S)-N-2-[(2'R)-2'-[2"-(Hydroxyamino)-2"-(oxo)ethyl]-6'-(oxo)-6'(oxo)-6'-(propylamino)hexanoyl]amino-3,3-dimethylbutanoic acid N-methylamide;

i) N-[(2R)-2-[(1'S)-1'-(Methyl)-2'-(hydroxyamino)-2'-(oxo)-ethyl]-6-(phenylmethoxy)hexanoyl]-L-phenylalanine N-methylamide;

j) N-[(2R)-2-[(1'S)-1'-(Methyl)-2'-(hydroxyamino)-2'-(oxo)-ethyl]-6-(oxo)-6-(propylamino)hexanoyl]-L-phenylalanine N-methylamide;

k) (2S)-N-2[(2'R)-[(1"R)-1"-(1,3-dihydro-1,3-dioxo-2H-isoindol-2-yl)methyl-2"-(hydroxyamino)-2"-(oxo)ethyl]-6'-(phenylmethoxy)hexanoyl]amino-3,3-dimethylbutanoic acid N-methylamide;

l) N-[(2R)-2-[2'-(Hydroxyamino)-2'-(oxo)ethyl]-6-(oxo)-6-(propylamino)hexanoyl]-L-phenylalanine N-2-phenylethylamide;

m) (2S)-N-2-[(2'R)-2'-[(1"S)-1"-(Methyl)-2"(hydroxyamino)-2"-(oxo)ethyl]-6-(phenylmethoxy)hexanoyl]amino-3,3-dimethylbutanoic acid N-2-phenylethylamide;

n) (2S)-N-2-[(2'R)-2'-[(1"S)-1"-(Methyl)-2"-(hydroxyamino)-2"-(oxo)ethyl]-6'-(oxo)-6'-(propylamino)hexanoyl]amino-3,3-dimethylbutanoic acid N-2-phenylethylamide;

o) (2S)-N-2-[(2'R)-2'-[(1"S)-1"-(Methyl)-2"-(hydroxyamino)-2"-(oxo)ethyl]-6'-(oxo)-6'-(propylamino)hexanoyl]aminno-3,3-dimethylbutanoic acid N-2-(4'-sulfamoyl)phenylethylamide;

p) (2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)phenylethylamide;

q) N-[(2R)-2-[2'-(Hydroxyamino)-2'-(oxo)ethyl]-6'-(phenylmethoxy)hexanoyl]-L-(3,5-dimethyl)phenylalanine N-2-(4'-sulfamoyl)phenylethylamide;

r) (2S)-N-2'-[(2'R)-2'-[2"-(hydroxyamino)-2"-(oxo)ethyl]-6'-[(4-methoxy)phenoxy]hexanoyl]amino-3,3-dimethylbutanoic acid N-2-(4'-sulfamoyl)phenylethylamide;

s) (2S)-N-2'-[(2'R)-2'-[2"-(hydroxyamino)-2"-(oxo)ethyl]-6'-[(4-methyl)phenoxy]hexanoyl]amino-3,3-dimethyl-butanoic acid N-2-(4'-sulfamoyl)phenylethylamide;

t) (2S)-N-2'-[(2'R)-2'-[2"-(Hydroxyamino)-2"-(oxo)ethyl]-6'-[(1-oxo)butylamino]hexanoyl]amino-3-cyclohexylpropionic acid N-2-[(2'R)-2'-[(1"-S)-1"-(Methyl)-2"-(hydroxyamino)-2"-(oxo)ethyl]-6-(phenylmethoxy)hexanoyl]amino-3,3-dimethylbutanoic acid N-methylamide;

v) (2S)-N-2-[(2'R)-2'-[(1"S)-1"-(2-Methylpropyl)-2"-(hydroxyamino)-2"-(oxo)ethyl]-6-(phenylmethoxy)hexanoyl]-amino 3,3-dimethylbutanoic acid N-methylamide;

w) N-[(2R)-2-[2'-(Hydroxyamino)-2'-(oxo)ethyl]-6-(phenoxy)-hexanoyl]-L-phenylalanine N-methylamide;

x) N-[(2R)-2-[2'-(Hydroxyamino)-2'-(oxo)ethyl]-7-(phenoxy)-heptanoyl]-L-phenylalanine N-methylamide;

y) (2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-phenylethylamide;

z) (2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-(4'-sulfamoyl)phenylethylamide;

aa) N-[(2R)-2-[2'-(hydroxyamino)-2'-(oxo)ethyl]-5-(phenylmethoxy)pentanoyl]-L-phenylalanine N-methylamide;

ab) N-[(2R)-2-[2'-(Hydroxyamino)-2'-(oxo)ethyl]-7-(phenylmethoxy)heptanoyl]-L-phenylalanine N-methylamide;

ac) N-[(2R)-2-[2'-(Hydroxyamino)-2'-(oxo)ethyl]-6-(phenyloxy)hexanoyl]-L-phenylalanine N-methylamide;

ad) N-[(2R)-2-[2'-(Hydroxyamino)-2'-(oxo)ethyl]-7-[(phenyloxy)heptanoyl]-L-phenylalanine N-methylamide;

ae) (2S)-N-2'-[(2'R)-2'-[2"-(Hydroxyamino)-2"-(oxo)ethyl]-6'-[(2-phenethylamino)-6'-(oxo)hexanoyl]amino-3,3-dimethylbutanoic acid N-methylamide;

af) (2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

ag) (2S)-N-2'-[(2'R)-2'-[2"-(Hydroxyamino)-2"-(oxo)ethyl]-6'-[(4-chlorophenoxy)hexanoyl]amino-3,3-dimethylbutanoic acid N-methylamide;

ah) (2S)-N-2'-[(2'R)-2'-[2"-(Hydroxyamino)-2"-(oxo)ethyl]-6'-[(3-methylphenoxy)hexanoyl]amino-3,3-dimethylbutanoic acid N-methylamide; and ai) (2S)-N-2'-[(2'R)-2'-(carboxymethyl)-6'-(3-methylphenoxy)hexanoyl]amino-3,3-dimethylbutanoic acid N-methylamide.

Compounds of the invention may be prepared by any suitable method known in the art and)or by the following process, which itself forms part of the invention.

According to another aspect of the invention, there is provided a process for preparing compounds of the invention as defined above.

The following is a schematic for the preparation of a common intermediate used to prepare compounds of the invention by various routes.

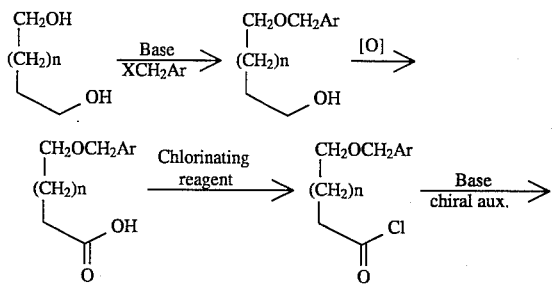

7
-continued
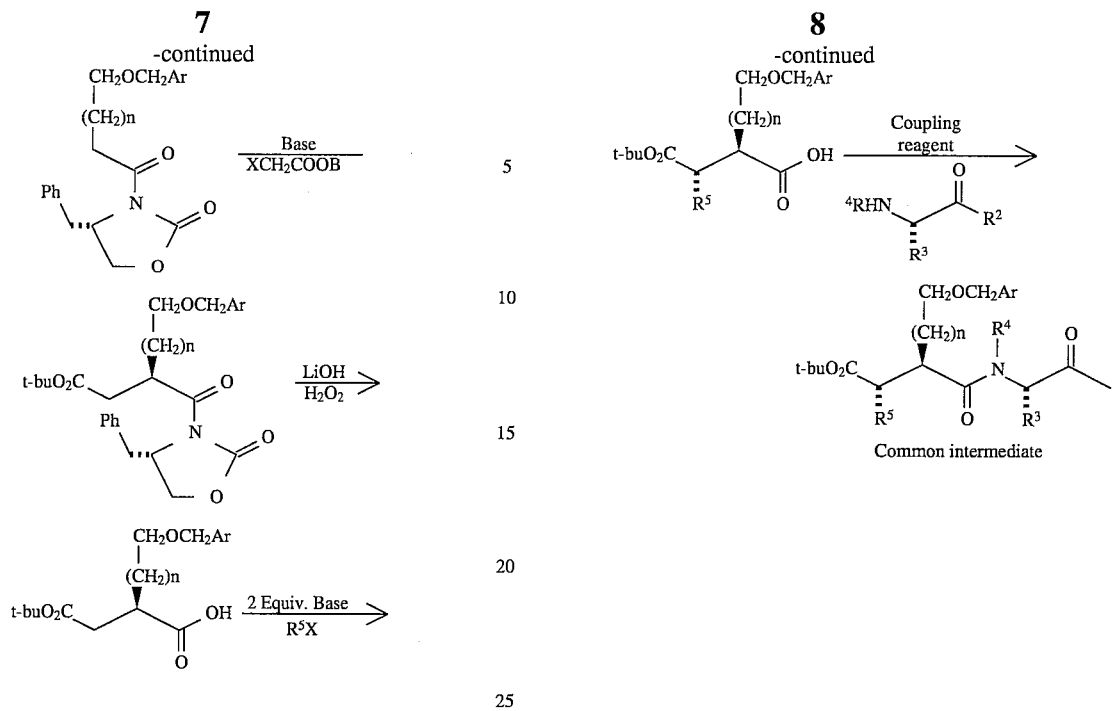
8
-continued
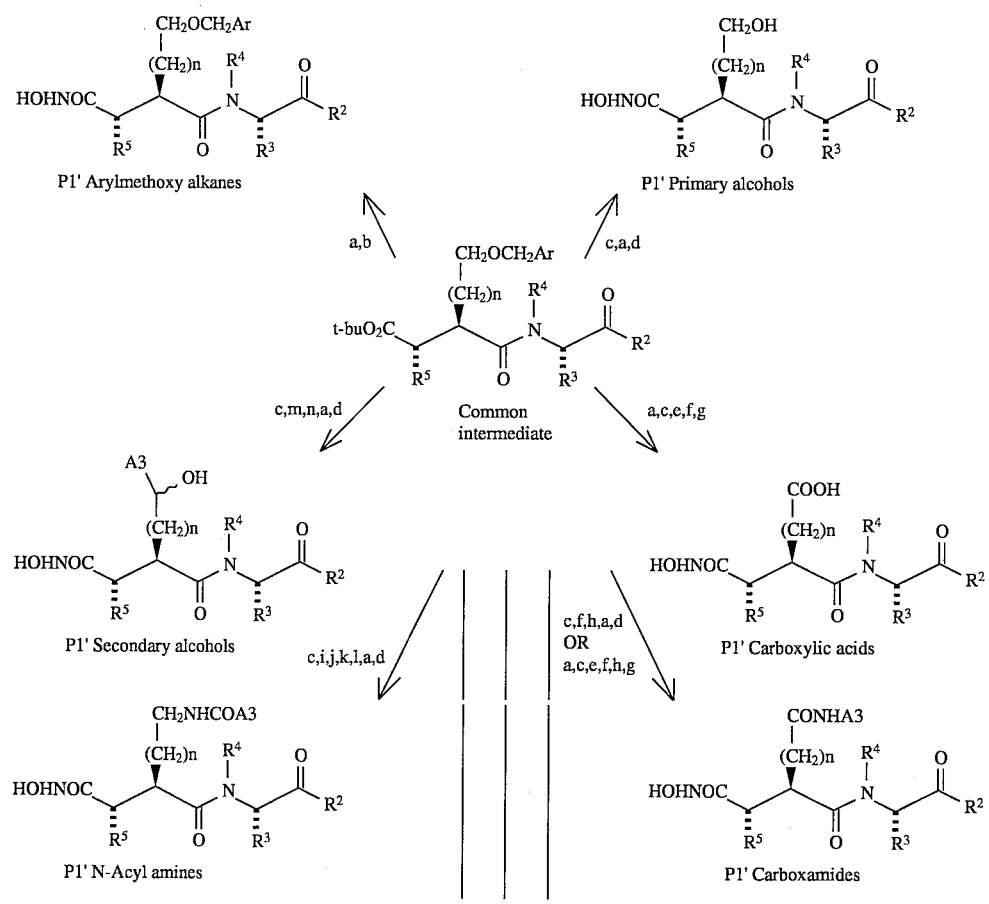

-continued
Synthesis of compounds of the invention from the common intermediate
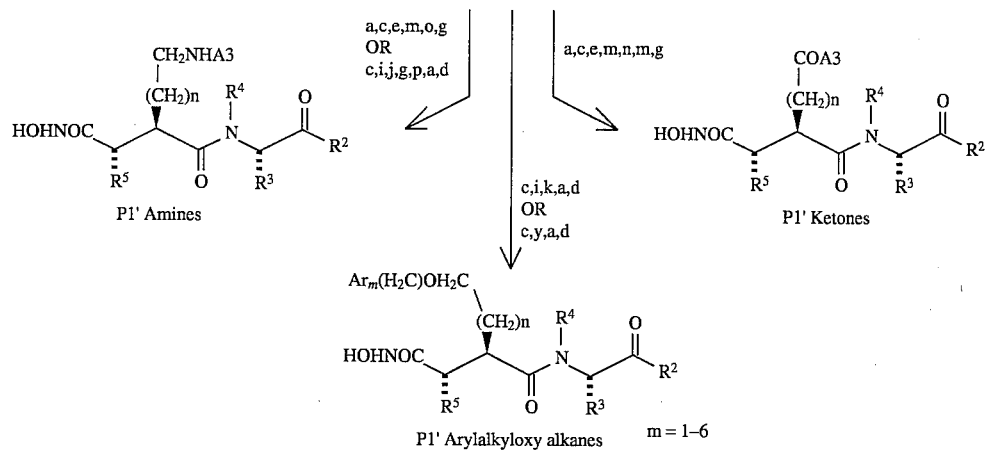
Synthesis of other compounds of the invention from the common intermediate.
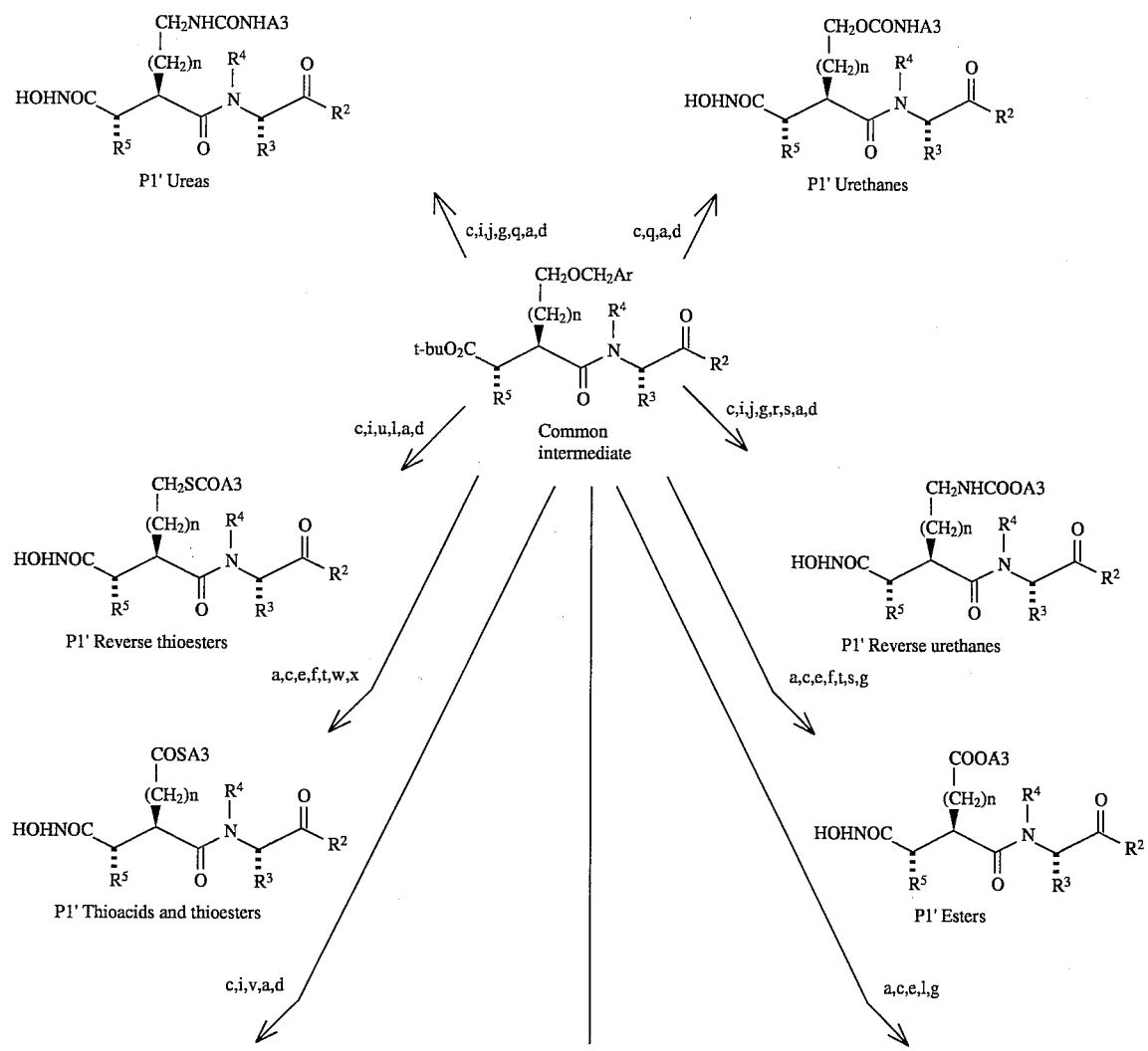

-continued
Synthesis of other compounds of the invention from the common intermediate.

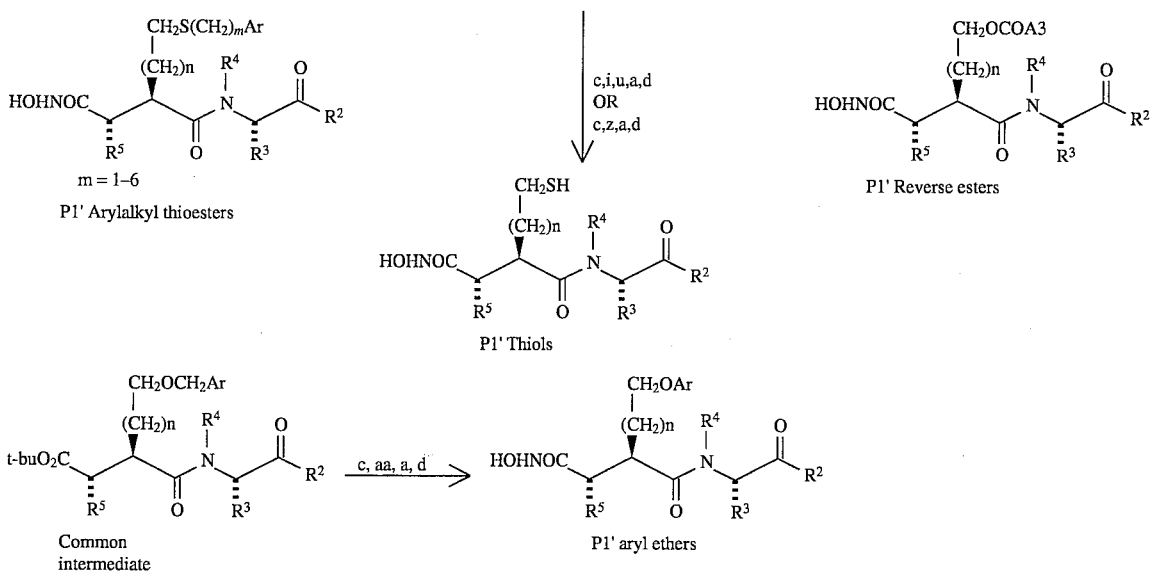

a) TFA
b) i) Isobutylchloroformate, NMM, TMSONH$_2$, H$_2$O
c) Hydrogenolysis
d) i) Isobutylchloroformate, NMM, TMSONH$_2$ ii) H$_2$O OR i) isobutylchloroformate, NMM, BzONH$_2$ ii) 5% Pd—C, H$_2$
e) Isobutylchloroformate, NMM, BzONH$_2$
f) Oxidation
g) Cat. H$_2$
h) Coupling with A3NH$_2$, where A3 is not H
i) MsCl
j) NaN$_3$
k) Ar(CH$_2$)$_m$O$^-$
l) Coupling with A3CoCl, where A3 is not H
m) PDC, CH2Cl$_2$
n) CH$_3$Ti(OCHMe$_2$)$_3$ OR A3Mgx, where A3 is not H
o) Reductive amination with NH$_4$OAc (Primary amine) or A3NH$_2$ (secondary amine), where A3 is not H
p) Reductive amination with A3CHO or alkylation with A3X, where A3 is not H
q) A3NCO, where A3 is not H
r) COCl$_2$ or Triphosgene
s) A3OH, where A3 is not H
t) (COCl)$_2$
u) NaSH
v) Ar(CH$_2$)$_m$S$^-$
w) A3S
x) Cat. H$_2$, with repeated additions of catalyst
y) Base, Ar(CH$_2$)$_m$X
z) i) PPh$_3$, i-proOCN=NCO-i-pro, CH$_3$COSH ii) LiOH
aa) PPh$_3$, DEAD, ArOH In a further aspect of the invention there is provided the use of a compound of invention in medicine, particularly in a method of treatment of diseases in which collagenolytic activity is important.

In another aspect of the invention there is provided the use of a compound of the invention in the preparation of an agent for the treatment of diseases in which collagenolytic activity is important.

The invention also provides a pharmaceutical composition comprising one or more compounds of the invention in association with one or more non-toxic pharmaceutically acceptable carriers and)or diluents and)or adjuvants. Other active ingredients may also be included in the compositions of the invention.

The compositions of the present invention may be formulated for administration by any route depending on the disease being treated. The compositions may be in the form of tablets, capsules, powders, granules, lozenges, liquid or gel preparations, such as oral, topical, or sterile parental solutions or suspensions.

Tablets and capsules for oral administration may be in unit dose presentation form, and may contain conventional excipients. Examples of these are binding agents such as syrup, acacia, gelatin, sorbitol, tragacanth, and polyvinylpyrollidone; fillers for example lactose, sugar, maize-starch, calcium phosphate, sorbitol or glycine; tableting lubricants, for example, magnesium sterate, talc, polyethylene glycol or ilica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents for example sorbitol, syrup, methyl cellulose, glucose syrup, gelatin, hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

The dosage unit involved in oral administration may contain from about 1 to 250 mg, preferably from about 25 to 250 mg. A suitable daily dose for a mammal may vary widely depending on the condition of the patient. However, a dose of about 0.1 to 300 mg)kg body weight, particularly from about 1 to 100 mg)kg body weight may be appropriate.

For topical application to the skin, the drug may be made up into a cream, lotion or ointment. Cream or ointment formulations that may be used for the drug are conventional formulations well known in the art, for example, as described in standard text books of pharmaceutics such as the British Pharmacopoeia.

For topical applications to the eye, the drug may be made up into a solution or suspension in a suitable sterile aqueous or non-aqueous vehicle. Additives, for instance buffers such as sodium metabisulphite; preservatives including bactericidal and fungicidal agents, such as phenyl mercuric acetate or nitrate, benzalkonium chloride or chlorohexidine, and thickening agents such as hydrocellulose may also be included.

The dosage employed for the topical administration will, of course, depend on the size of the area being treated.

The active ingredient may also be administered parenterally in a sterile medium. The drug depending on the vehicle and concentration used, can either be suspended or dissolved in the vehicle. Advantageously, adjuvants such as local anaesthetic, preservatives and buffering agents can be dissolved in the vehicle.

For use in the treatment of rheumatoid arthritis, the compounds of this invention can be administered by the oral route or by injection intra-articularly into the affected joint. The daily dosage for a 70 kg mammal will be in the range of 1 mgs to 1 gram.

The following examples illustrate the invention, but are not intended to limit the scope in any way.

EXAMPLE 1

PREPARATION OF INTERMEDIATES

1a. Synthesis of 6-Phenylmethoxyhexane-1-ol.

Hexane-1,6-diol [25 g, 0.21 mol] is dissolved in dry)distilled THF (300 mL) under a $N_2$ atmosphere. 80% NaH [6.3 g, 0.21 mol] is then added with vigorous stirring in small portions over ~10–20 minutes. Evolution of gas ($H_2$)is noted. The reaction is heated to reflux with continued vigorous stirring for 4.5 hours resulting in the formation of a thick gray-colored solid. Benzyl bromide [25 mL, 0.21 mol] is added in one portion, and the reaction is allowed to reflux for ~22 hours. The solid mass is replaced by a white-colored solid (NaBr) which is filtered from the reaction after cooling to room temperature. The solid is washed with THF and the combined filtrates are evaporated, leaving a yellow oil. The oil is taken up in $Et_2O$, and washed successively with distilled water until there is no indication of the starting diol (as determined by TLC) and then washed with brine. The organic layer is dried over $Na_2SO_4$ and the $Et_2O$ is evaporated. The resulting oil is a mixture of the di-and mono-benzylated hexanol (approximately a 2:1 ratio of mono to di-benzylated based on $^1H$- NMR data, 38.05 g, 60% yield). The mixture is used without further purification in the next step. Isolation of a small amount of mono benzylated product gives the following data; $^1H$- NMR ($CDCl_3$) : δ1.3–1.7 (m, 9H, —$(CH_2)_4$ and —OH), 3.5 (t, 2H), —$CH_2OCH_2Ph$), 3.64 (t, 2H, —$CH_2OH$), 4.5 (s, 2H, —$OCH_2Ph$), 7.3 (m, 5H, Ar).

1b. Synthesis of 6-Phenylmethoxyhexanoic acid

A solution of compound obtained in example 1a (38 g, 0.114 mol) in 50 mL of dry DMF is added dropwise to a solution of DMF (300 mL) containing pyridinium dichromate (128 g, 0.342 mol). The reaction is slightly exothermic and so is maintained at 10°–20° C. for the first few hours of the reaction. The reaction is stirred for 9 hours at room temperature. The reaction is diluted with 2.5 L $H_2O$ and extracted 10 times with EtOAc (150 ML) which is in turn washed with $H_2O$. Remaining PDC is removed by filtering the EtOAc extractions through anhydrous $MgSO_4$. The organic layer is then extracted with 1N NaOH (5 times). The combined basic extractions are washed with several portions of fresh EtOAc. The basic layer is then slowly acidified with concentrated HCl to a pH 2–3 and extracted 5 times with EtOAc. The combined organic layers are dried over $Na_2SO_4$ and the solvent is evaporated to afford pure acid (~75% yield).

$^1H$-NMR ($CDCl_3$) : δ1.45 (m, 2H, —$CH_2$), 1.65 (m, 4H, —$(CH_{22})$, 2.35 (t, 2H, —$CH_2COOH$), 3.37 (t, 3H, —$CH_2OCH_2Ph$), 4.5 (s, 2H, —$OCH_2Ph$), 7.3 (m, 5H, Ar).

1c. Synthesis of 6-phenylmethoxyhexanoyl chloride 30.52 g of the compound of Example 1b [0.14 mol] is dissolved in dry $CH_2Cl_2$ and cooled to 0° C. Oxalyl chloride [13.09 mL, 0.154 mol] is added in one portion. Some minor gas evolution ($CO_2$)is observed. ~5 drops of dry DMF is added with stirring and the gas evolution is noticeably more vigorous. The reaction is allowed to stir while warming to room temperature until no more bubbling if observed and then stirred ~30 minutes more. The solvent and remaining oxalyl chloride is removed under vacuum. A yellow oil with some solid dispersed in it remains. The oil is filtered through a dry filter, then is placed on high vacuum suction until used in the next step (29.6 g, 90+% yield).

$^1H$- NMR ($CDCl_3$) : δ1.37 (m, 2H), —$CH_2$), 1.7 (m, 4H, —$(CH_2)_2$), 2.9 (t, 2H, —$CH_2COCl$), 3.5 (t, 2H, —$CH_2OCH_2Ph$), 4.5 (s, 2H, —$OCH_2Ph$), 7.35 (m, 5H, Ar).

1d. Synthesis of (4S)-4-benzyl-3-[(6'-phenylmethoxy)hexanoyl]-2-oxazolidone (S)-(–)-4-benzyl-2-oxazolidinone [21.08 g, 0.12 mol] is dissolved in dry)distilled THF (250 mL) under a $N_2$ atmosphere and cooled to –78° C. A solution of 1.6M n-butyl lithium in hexane (n-BuLi) [74.77 mL, 0.12 mol] is added dropwise with stirring while maintaining the reaction between –65° C. to –78° C. Near the end of this addition, the reaction is observed to turn a deeper yellow color, indicating benzylic protons being deprotonated and that enough n-BuLi has been added. The reaction is allowed to stir at –78° C. for 25 minutes, then 28.8 g of the compound of example 1c [0.12 mol] in THF (100 mL) is added dropwise, maintaining the reaction near –78° C. The deep yellow color of the reaction lightens with the addition. The reaction is allowed to gradually warm to room temperature and then is quenched with the addition of a saturated solution of $NH_4Cl$ (150 mL). The THF is evaporated and the residue is extracted into $Et_2O$ which is washed with 0.5N NaOH (5 times), $H_2O$, and finally brine. It is then dried over $Na_2SO_4$ and evaporated to an oil residue which is purified by flash column chromatography to give 46.5 g (85% yield).

$^1H$- NMR ($CDCl_3$) : δ1.5 (m, 2H, —$CH_2$), 1.7 (m, 4H, —$CH_2)_2$), 2.77 (dd, 1H, —$CHCH_2Ph$), 2.95 (m, 2H, —$CH_2CON$), 3.3 (dd, 1H, —$CHCH_2Ph$), 3.5 (t, 2H, —$CH_2OCH_2Ph$), 4.17 (m, 2H, ring —$CH_2$), 4.5 (s, 2H, —$OCH_2Ph$), 4.67 (m, 1H, ring —CH), 7.3 (m, 10H, Ar).

1e. Synthesis of (4S)-4-benzyl-3-[2'R)-2'-(tert-butoxy-carbonylmethyl)-6'-(phenylmethoxy)hexanoyl]-2-oxazolidone Diisopropylamine [1.82 mL, 13 mol] in dry)distilled THF (10 mL) is cooled to −15° C. under a $N_2$ atmosphere. A solution of 1.6M n-BuLi in hexane [8.12 mL, 13 mmol] is slowly added dropwise with stirring while maintaining the temperature below 0° C. The reaction is allowed to stir at 0° C. for 30 minutes and then cooled to −78° C. The product of example 1d [4.71 g, 12 mmol] in 50 mL THF is added dropwise with stirring while maintaining the temperature near −78° C. Stirring is continued for 30 minutes. A solution of t-butyl bromoacetate [1.8 mL, 12 mmol] in THF (25 mL) is then added dropwise at −78° C. Following addition, the reaction is allowed to warm to room temperature and then quenched cautiously with $H_2O$. The THF is evaporated and the residue extracted into EtOAc. The organic layer is washed with 5% $NaHCO_3$, 5% citric acid, and brine, and then dried over $Na_2SO_4$. The solvent is evaporated, and the resulting oil solidified on standing. The solid product is recrystalized with EtOAc)hexane several times, or alternatively, flash chromatography is used. This affords 3.21 g of a white fluffy crystal (55% yield).

$^1$H- NMR (CDCl$_3$) : δ1.4–1.72 (s and m, 15H, t-butyl and —(CH$_2$)$_3$, 2.48 (dd, 1H, —COCH$_2$CHCO), 2.75 (overlapping dd, 2H, one —CHCH$_2$CHCO and one —CHCH$_2$Ph, 3.34 (dd, 1H, —CHCH$_2$Ph), 3.45 (t, 2H, —CH$_2$OCH$_2$Ph), 4.15 (m, 3H, ring —CH$_2$ and —CH$_2$CHCO), 4.48 (s, 2H, —OCH$_2$Ph), 4.63 (m, 1H, ring —CH), 7.3 (m, 10H, Ar).

1f. Synthesis of (2R)-2-(tert-butyoxycarbonylmethyl)-6-(phenylmethoxy) hexanoic acid 0.5 g of the compound of Example 1e is dissolved in 15 mL of a 4:1 THF)H$_2$O solution and cooled to about 0° C., but not below, under a N$_2$ atmosphere. Slowly, dropwise and with stirring, 30% aqueous H$_2$O$_2$ [0.5 mL, 4.4 mmol] is added. After stirring 5 minutes, a solution of LiOH.H$_2$O [0.07 g, 1.5 mmol] in 2 mL H$_2$O is added dropwise. Some gas evolution is observed. The reaction is warmed slowly to room temperature and stirred for 1 hour, then a solution of Na$_2$SO$_3$ [0.2 g, 1.7 mmol] in 2 mL H$_2$O is added dropwise. Some heat is evolved during this process, so the reaction is cooled with an ice bath. After stirring ~20 minutes the THF is evaporated (below 30° C.) and the basic, aqueous mixture remaining is extracted with EtOAc (5 times). These combined extracts contain the free benzyl oxazolidinone which can be recrystalized and recycled for further use.

The basic layer is then cooled and acidified with the slow addition of concentrated HCL to a pH 2–3. The cloudy mixture is then extracted 5 times with EtOAc, dried over Na$_2$SO$_4$ and evaporated to give 0.29 g of pure acid (86% yield).

$^1$H- NMR (CDCl$_3$) : δ1.42–1.7 (s and m, 15H, 5-butyl and —(CH$_2$)$_3$), 2.37 (dd, 1H, —COCH$_2$CHCO), 2.6 (dd, 1H, —COCH$_2$CHCO), 2.8 (m, 1H, —COCH$_2$CHCO), 3.45 (t, 2H, —CH$_2$OCH$_2$Ph), 4.5 (s, 2H, —OCH$_2$Ph), 7.3 (m, 5H, Ar).

1g. Synthesis of N-[(2R)-2-tert-butoxycarbonylmethyl)-6-(phenylmethoxy) hexanoyl]-L-phenylalanine N-methylamide A solution of the product of Example 1f (3.36 g, 0.01 mol) and L-phenylalanine N-methylamide TFA salt (2.9 g, 0.01 mol) in dry dimethylformamide (40 mL) under nitrogen are cooled to −6° C. and treated dropwise with diethylcyanophosphonate (1.63 g, 0.01 mol) followed by triethylamine (3.03 g, 0.03 mol). The reaction mixture is stirred at 0° C. for 1 hour, warmed to room temperature over 1 hour, and then stirred for two additional hours. The reaction mixture is diluted with water and extracted with ethyl acetate. The combined ethyl acetate layers are sequentially washed with 5% citric acid, saturated sodium bicarbonate, water, and brine. The ethyl acetate is separated, dried (Na$_2$SO$_4$), and evaporated. The residue is purified by silica gel columnchromatography using 50–70% ethyl acetate in hexanes as the eluent. The appropriate fraction yielded 4.21 g of the product (85%).

$^1$H NMR (CDCl$_3$) δ1.20–180 (m, 15H, CCH$_2$CH$_2$CH$_2$C and t-butyl H), 2.25–2.60 (m, 3H, CH$_2$CO and CHCO), 2.65 (d, 3H, NCH$_3$), 3.38 (t, 2H, CCH$_2$O), 3.07 (d, 2H, ArCH$_2$C), 4.44 (s, 2H, OCH$_2$Ar), 4.57 (q, 1H, NCH), 6.34 (q, 1H, NH), 6.52 (d, 1H, NH), 7.20–7.60 (m, 10H, ArH).

EXAMPLE 2

N-[(2R)-2-[2'-(Hydroxyamino)-2'(oxo)ethyl]-6-(phenylmethoxy)hexanoyl]-L-phenylalanine N-methylamide 2a. Synthesis of N-[(2R)-2-(carboxymethyl)-1-(phenylmethoxy)hexanoyl]-L-phenylalanine N-methylamide A solution of the compound formed in Example 1g (0.33 g, 0.66 mmol) in trifluoroacetic acid (7 mL) and water (3 mL) is stirred at room temperature for 6 hours. The solvents are removed on a rotary evaporator. The residue is treated with acetonitrile and evaporated (three times) in order to azeotrope water. The crude product is placed on a high vacuum pump for 2 hours to give a gummy material, which is triturated with diethyl ether to produce a colorless solid. The solid was collected by filtration and air dried. (0.227 g), 78% yield).

$^1$H NMR (MeOH-d$_4$) δ0.80–1.50 (m, 6H, CCH$_2$CH$_2$CH$_2$C), 2.00–2.60 (m, 6H, NCH$_3$, CH$_2$CO and CHCO), 2.74 (dd) and 2.92 (dd), (2H, CCH$_2$Ar), 3.20 (t, 2H, OCH$_2$C), 4.25 (m, OCH$_2$Ar and NCH), 6.90–7.30 (m, 10H, ArH).

2b.

Under nitrogen atmosphere, the carboxylic acid formed in Example 2a (0.44 g, 1.0 mmol) is dissolved in dry tetrahydrofuran (20 mL), and treated with N-methyl morpholine (0.13 g, 1.15 mmol) via syringe. The reaction mixture is cooled to −10° C. and treated with isobutylchloroformate (0.15 mL, 1.15 mmol) via syringe. After stirring the suspension for 20 minutes, O-(trimethylsilyl)hydroxylamine (0.12 mL, 1.15 mmol) is added via syringe and the reaction mixture is stirred in the cold for 3 hours. The ice bath is removed, the reaction mixture is filtered, and the filtrate is evaporated to a colorless solid. The solid is triturated with methylene chloride, collected by filtration, and air dried to give 0.27 g of a colorless solid (59% yield).

$^1$H NMR (MeOH-d$_4$) δ1.6–1.1 (m, 6H, CCH$_2$CH$_2$CH$_2$C), 2.22 (dd, 1H) and 2.10 (dd, 1H) CH$_2$CON, 2.60 (m, 1H, CH$_2$CHCO), 2.64 (d, 3H, NHCH$_3$), 3.15 (dd, 1H) and 2.96 (dd, 1H, OCH$_2$Ar), 3.40 (t, 2H, CH$_2$OCH$_2$Ar), 4.46 (s, 2H, ArCH$_2$O), 4.49 (M, 1H, NCHCO), 7.35–7.10 (m, 10H), 7.90 (m, 1H), 8.20 (d, 1H).

EXAMPLE 3

N-[(2R)-2-[2'-(hydroxyamino)-2'-(oxo)ethyl]-6-(hydroxy)hexanoyl]-L-phenylalanine N-methylamide 3a. Synthesis of N-[(2R)-2-(tert-butoxycarbonylmethyl)-6-(hydroxy)hexanoyl]-L-phenylalanine N-methylamide Under nitrogen atmosphere, a solution of the compound formed in Example 1g (2.5 g, 0.005 mol) in methanol (50 mL) is treated with ammonium formate (2.5 g) and 10%

Pd)C (1.0 g). The mixture is heated to reflux for 4 hours at which point 2.5 g of ammonium formate is added and refluxing is continued for 2 hours. The heat is removed and the reaction mixture is allowed to stand overnight at room temperature. After 15 hours, ammonium formate (2.5 g) and 10% Pd)C (0.2 g) are added and the reaction mixture is heated at reflux for 4 hours. The reaction mixture is cooled and the catalyst is collected via filtration. The filtrate is evaporated to dryness and the residue is partitioned between water and ethyl acetate. The ethyl acetate layer is washed with water, then dried ($Na_2SO_4$), filtered, and evaporated. The product is purified by silica gel column chromatography using 5% methanol in ethyl acetate as the eluent, (1.3 g, 64% yield).

$^1$H NMR (CDCl$_3$) δ1.00–1.70 (m, 15H, CCH$_2$CH$_2$CH$_2$C and t-butyl H), 2.25–2.60 (m, 3H), 2.69 (d, 3H, NCH$_3$), 3.00–3.20 (m, 2H, CH$_2$Ar), 3.50–3.70 (m, 2H, CH$_2$O), 4.56 (q, 1H, NCH), 6.15 (m, 1H, NH), 7.13 (d, 1H, NH), 7.15–7.45 (m, 5H, ArH).

3b. Synthesis of N-[(2R)-2-(Carboxymethyl)-6-(hydroxy)-Hexanoyl]-L-phenylalanine N-methylamide The product formed in Example 3a (0.7 g, 1.72 mmol) is dissolved in 10 mL of a 7:3 trifluoroacetic acid-water mixture and stirred at room temperature for 4.5 hours. The solvents are removed on a rotary evaporator and the residue is treated with acetonitrile and evaporated (three times) in order to azeotrope water. The colorless solid is dried on a high vacuum pump for 4 hours, then triturated with diethyl ether. The colorless solid is collected by filtration and dried. (0.6 g, 100% yield).

$^1$H NMR (MeOH-d$_4$) δ0.88–1.60 (m, 6H, CCH$_2$CH$_2$CH$_2$C), 2.15–2.60 (m, 6H, NCH$_3$, CH$_2$CO and CHCO), 2.75 (dd) and 2.90 (dd) (2H, CH$_2$Ar), 4.10 (t, 2H, CH$_2$O), 4.30 (q, 1H, NCH), 6.90–7.30 (m, 5H, ArH), 7.58 (m, 1H, NH), 8.00 (d, 1H, NH).

3c.

Under nitrogent atmosphere, the product of example 3b (0.245 g, 0.7 mmol) is dissolved in dry tetrahydrofuran (20 mL), cooled to −15° C. and treated with N-methylmorpholine (0.14 g, 1.33 mmol). After 5 minutes, isobutylchloroformate (0.18 g, 1.33 mmol) is added dropwise and the reaction mixture is stirred for 15 minutes. O-(trimethylsilyl)hydroxylamine (0.42 g, 3.9 mmol) is added dropwise. The reaction mixture is stirred at −15° C. for 1 hour, followed by 1 hour at 0° C., then 30 minutes at room temperature. The reaction mixture is filtered and the filtrate is evaporated to dryness. The residue is triturated first with diethyl ether followed by methylene chloride. The solid is collected by filtration and purified by preparative thin-layer chromatography using 15% methanol in methylene chloride as eluent, giving a colorless solid. (0.12 g, 25% yield).

$^1$H NMR (MeOH-d$_4$) δ0.80–1.50 (m, 6H, CCH$_2$CH$_2$CH$_2$C), 1.80–2.10 (m, 2H, CH$_2$CO), 2.30–2.44 (m, 1H, CHCO), 2.47 (s, 3H, NCH$_3$), 2.95 (dd) and 2.72 (dd) (2H, ArH), 3.25 (t, 2H, CH$_2$O), 4.30 (g, 1H, NCH), 6.90–7.30 (m, 5H, ArH).

Mass (FAB) : 366 (MH$^+$)

EXAMPLE 4

N-[(2R)-2-[2'-(Hydroxyamino)-2'-(oxo)ethyl]-5-(carboxy)pentanoyl]-L-phenylalanine N-methylamide 4a. Synthesis of N-[(2R)-2-[2'-(Phenylmethoxyamino)-2'-(oxo)ethyl]-6-(hydroxy)hexanoyl]-L-phenylalanine N-methylamide Under nitrogen atmosphere, the carboxylic acid product formed in Example 3b (0.035 g, 0.1 mmol) is dissolved in anhydrous dimethylformamide (1 mL) and treated with N-methylmorpholine (0.017 mL, 0.15 mmol). The reaction is cooled to −10° C. and treated dropwise with isobutylchloroformate (0.02 mL, 0.15 mmol). The reaction is stirred for 20 minutes, then a suspension of O-benzylhydroxylamine hydrochloride (0.024 g, 0.15 mmol) and N-methylmorpholine (0.017 mL, 0.15 mmol) in dimethylformamide (1.5 mL) is added. After stirring 20 minutes, the ice bath is removed and the reaction mixture is stirred for 3 hours. The dimethylformamide is removed on a rotary evaporator and the residue is dissolved in ethyl acetate. The ethyl acetate is washed with 5% citric acid and 5% sodium bicarbonate, then dried ($Na_2SO_4$), filtered, and evaporated. The solid is triturated with diethyl ether and collected by filtration to give 10 mg (2% yield) of compound.

$^1$H NMR (MeOH-d$_4$) δ1.6-1.1 (m, 6H, CCH$_2$CH$_2$CH$_2$C), 2.13 (m, 2H, CH$_2$CHCO), 2.67 (m, 1H, CH$_2$CHCO), 2.69 (d,3H, NCH$_3$), 3.15 (dd) and 2.94 (dd), (2H, CH$_2$Ar), 3.48 (t, 2H, CH$_2$OH), 4.50 (m, 1H, NCHCO), 4.80 (s, 2H, ArCH$_2$O), 7.4–7.17 (m, 10H, Ar), 7.94 (m, 1H, NH), 8.24 (d, 1H, NH).

4b. Synthesis of N-[(2R)-2-[2'-(Phenylmethoxyamino)-2'-(oxo)ethyl]-5-(carboxy)pentanoyl ]-L-phenylalanine N-methylamide A solution of the compound of Example 4a (0.05 g, 0.11 mmol) in dimethylformamide (1 mL) is treated with pyridinium dichromate (0.144 g, 0.38 mmol) at room temperature overnight. The reaction mixture is partioned between ethyl acetate and water. The aqueous layer is separated and extracted with ethyl acetate. The ethyl acetate extracts are combined, dried ($Na_2SO_4$), filtered, and evaporated to a gum. Trituration with diethyl ether produces an off-white solid (0.023 g, 45% yield).

$^1$H NMR (MeOH-d4) δ1.6-1.1 (m, 6H, CCH$_2$CH$_2$CH$_2$C), 2.27-2.02 (m, 4H, CH$_2$CHCO and CH$_2$COOH), 2.70 (m, 4H, NCH$_3$ and CH$_2$CHCO), 3.15 (dd) and 2.92 (dd), (2H, CH$_2$Ar), 4.55 (m, 1H, NCHCO), 4.80 (s, 2H ArCH$_2$O), 7.43-7.10 (m, 10H, Ar), 7.91 (m, 1H, NH), 8.24 (d, 1H, NH).

4c.

A solution of the compound formed in Example 4b (0.023 g, 0.049 mmol) in ethanol (5 mL) is treated with 10% Pd)C (0.010 g) and pyridine (2 drops) under hydrogen atmosphere. After 32 hours, the reaction mixture is filtered to removed catalyst and the filtrate evaporated to a yellow oil and placed under high vacuum to give a gum. Trituration with diethylether produces an off-white solid, which is collected by filtration and dried under a nitrogen flow to give the final compound.

$^1$H NMR (MeOH-d4)67 1.91-1.35 (m, 6H, CCH$_2$CH$_2$CH$_2$C), 2.30-2.10 (m, 4H, CH$_2$CHCO and CH$_2$COOH), 2.62 (m, 1H, CH$_2$CHCO), 2.70 (s, 3H, NCH$_3$), 3.15 (m) and 2.95 (m), (4H), 4.52 (t, 1H, NCHCO), 7.36-7.15 (m, 5H, Ar).

EXAMPLE 5

N-[(2R)-2-[2'-(Hydroxyamino)-2'-(oxo)ethyl]-6-(propylamino)-6-(oxo)hexanoyl]-L-phenylalanine N-methylamide 5a. Synthesis of N-[(2R)-2-(tert-Butoxycarbonylmethyl)-5-(carboxy)pentanoyl]-L-phenylalanine N-methylamide Pyridinium dichromate (0.658 g, 1.7 mmol) is added to a solution of the compound formed in Example 3a (0.203 g, 0.5 mmol) in DMF (2 mL) under a nitrogen atmosphere. The resulting mixture is stirred at room temperature for 16 hours. The reaction mixture is diluted with water and extracted with ethyl acetate. The combined ethyl acetate layers are washed with water and brine. The ethyl acetate is separated, dried (Na₂SO₄), and evaporated. The gummy crude product (0.18 g) without any further purification is used in the next step.

¹H NMR (CDCl₂) δ1.10–1.80 (m, 13H, CCH₂CH₂C, t-butyl H), 2.20–2.80 (m, 8H), 3.00–3.20 (m, 2H), 4.68 (q, 1H, NCH), 6.50 (s, 1H), 7.00–7.60 (m, 5H, ArH).

5b. Synthesis of N-[(2R)-2-(tert-Butoxycarbonylmethyl)-6-(propylamino)-6-(oxo)hexanoyl]-L-phenylalanine N-methylamide A solution of the acid of example 5a (0.18 g, 0.43 mmol) and n-propylamine (0.1 g, 1.7 mmol) in dry DMF (5 mL) under nitrogen is cooled to –5° C. and treated dropwise with diethylcyanophosphonate (0.07 g, 0.43 mmol) followed by triethylamine (0.86 g, 0.85 mmol). The reaction mixture is stirred at 0° C. for 1 hour, then slowly allowed to come to room temperature during 1 hour. The reaction mixture is stirred at room temperature for 3 hours, then diluted with water and extracted with ethyl acetate and ether solvents. The combined organic layers are sequentially washed with 5% citric acid, saturated NaHCO₃, water, and brine. The organic layer is separated, dried (Na₂SO₄), and evaporated. The residue is triturated with diethyl ether to produce a white solid. The solid is collected by filtration and air dried to give 0.065 g. The overall yield for two steps is 28.3%

¹H NMR (CDCl₃) δ0.91 (t, 2H, CH₂CH₃), 1.30–1.80 (m, 15H, CCH₂CH₂C, CH₂CH₃, t-butyl H), 2.13 (t, 2H, CH₂CON), 2.25–2.60 (m, 3H, CH₂COO and CHCO), 2.71 (d, 3H, NCH₃), 3.05–3.30 (m, 4H, NHCH₂Ar and CH₂Ar), 4.62 (g, 1H, NCH), 5.98 (br signal, 1H, NH), 6.38 (br signal, 1H, NH), 6.70 (br signal, 1H, NH), 7.10–7.40 (m, 5H, ArH).

5c. Synthesis of N-[(2R)-2-(Carboxymethyl-6-(propylamino)-6-(oxo)hexanoyl]-L-phenylalanine N-methylamide A solution of the compound formed in example 5b (0.06 g, 0.13 mmol) in trifluoroacetic acid (3.5 mL), and water (1.5 mL) is stirred at room temperature for 4 hours. The solvents are removed on a rotary evaporator. The residue is treated with acetonitrile and evaporated (three times) in order to azeotrope water. The whie solid obtained is placed on a high vacuum pump for 1 hour. The product is triturated with diethyl ether. The product is collected by filtration and air dried to give 0.045 g (85.4% yield) of a white solid.

¹H NMR (MeOH-d₄) δ0.70 (t, 2H, CH₂CH₃), 1.10–1.5 (m, 6H, CH₂CH₃ and CCH₂CH₂C), 1.91 (t, 2H, CH₂CON), 2.05–2.60 (m, 6H, CH₂COO, CHCO and NCH₃), 2.70–3.00 (m, 4H, NHCH₂ and CH₂Ar), 4.30 (q, 1H, NCH), 6.90–7.30 (m, 5H, ArH), 7.60 (m, 1H), 8.00 (d, 1H).

Mass (FAB) : 406 (MH⁺)

5d.

Under a nitrogen atmosphere, the carboxylic acid compound formed in example 5c (0.04 g, 0.1 mmol) in dry THF (10 mL) is cooled to –15° C. (solubility of the acid seems to be low in THF, at low temperature some acid precepitated out) and treated with N-methylmorpholine (0.02 g, 0.2 mmol). After five minutes, isobutylchloroformate, (0.027 g, 0.2 mmol) is added dropwise and the reaction mixture is stirred for 35 minutes. O-(trimethylsilyl)hydroxylamine (0.126 g, 1.2 mmol) is added dropwise. The reaction mixture is stirred at –15° C. for 1 hour, followed by 1 hour at 0° C., then 1.5 hours at room temperature. The reaction mixture is filtered and the precipitate washed several times with dichloromethane. The residue is once again taken into dichloromethane and stirred for 2 hours. The white solid is collected by filtration and dried in vacuuo to give the final product.

¹H NMR (MeOH-d₄) δ0.70 (t, 3H, CH₂CH₃), 1.10–1.50 (m, 6H, CH₂CH₃ and CCH₂CH₂C), 1.80–2.10 (m, 4H, CH₂COO and CH₂CON), 2.30–2.60 (m, 4H, CHCO, NCH₃), 2.65–3.05 (m, 4H, NHCH₂ and CH₂Ar), 4.30 (d, 1H, NCH), 6.90–7.30 (m, 5H, ArH).

Mass (FAB) : 421 (MH⁺)

EXAMPLE 6

N-[(2R)-2-[2'-(Hydroxyamino)-2'-(oxo)ethyl]-(6RS)-6-(hydroxy)heptanoyl]-L-phenylalanine N-methylamide 6a. Synthesis of (4S)-4-Benzyl-3-[(2'R)-2'-(tert-butoxycarbonylmethyl)-6'-(hydroxy)hexanoyl]-2-oxazolidone.

The compound of example 1e [1.5 g, 3 mmol] is dissolved in absolute ethanol and enough EtOAc to get the material into solution. 1 g of 20% Palladium Hydroxide on carbon (Pd(OH)₂)C) and 0.28 mL [30 mmol] of 1,4-cyclohexadiene are added, and the reaction is warmed slowly to 65° C. while stirring under a N₂ atmosphere. A vigorous frothing occurs shortly after (H₂ generation). The reaction is stirred for 12 hrs. The reaction is cooled and filtered through Celite, and the Celite is washed with EtOAc. The solvent is evaporated, and the residue solidified. The solid is recrystalized from Et₂O)hexane, which affords 1.04 g of a white fluffy solid product (85% yield).

¹H- NMR (CDCl₃) : δ1.4–1.8 (s and m, 16H, t-butyl, —OH, and —(CH₂)₃), 2.54 (dd, 1H, —COCH₂CHCO), 2.84 (overlapping dd, 2H, one —COCH₂CHCO and one —CHCH₂Ph), 3.4 (dd, 1H, —CHCH₂Ph), 3.68 (t, 2H, —CH₂OH), 4.22 (m, 3H, oxazol. ring —CH₂ and —CH₂CHCO), 4.72 (m, 1H, oxazol. ring —CH), 7.35 (m, 5H, Ar).

6b. Synthesis of (4S)-4-Benzyl-3-[(2'R)-2'-(tert-butoxy-carbonylmethyl)-5'-(formyl)pentanoyl]-2-oxazolidone Oxalyl chloride [0.231 mL, 2.7 mmol] is dissolved in 10 mL anhyd. CH₂Cl₂ and cooled to –78° C. under a N₂ atmosphere. 0.192 mL [2.7 mmol] of anhydrous dimethyl sulfoxide (DMSO) in 5 mL CH₂Cl₂ is added dropwise via syringe; this is accompanied by the evolution of CO₂ and CO bubbles. The reaction is stirred at –78° C. for 30 min. 1.0 g [2.46 mmol] of the compound of example 6a in 10 mL of CH₂Cl₂ is then added dropwise via syringe, which causes the reaction to become cloudy white. Stirring is continued for 1 hr. at –78° C., then 1.58 mL [11 mol] of triethylamine (Et₃N) in 10 mL of CH₂Cl₂ is added dropwise via syringe and the reaction warmed to room temperature. During this time, the reaction becomes increasingly clearer. The reaction is partitioned between H₂O and CH₂Cl₂ and the organic layer washed with 5% NaHCO₃, 5% citric acid, H₂O, and brine, then dried over Na₂SO₄. The solvent is removed and the residue is flash chromatographed to give 0.81 g of a gummy solid (81%).

¹H- NMR (CDCl₃) : δ1.4–1.8 (s and m, 13H, t-butyl and —(CH₂)₂), 2.54 (overlapping t and dd, 3H, —CH₂CHO and one —COCH₂CHCO), 2.8 (overlapping dd, 2H, one —COCH₂CHCO and one —CHCH₂Ph), 3.36 (dd, 1H, one —CHCH₂Ph), 4.2 (m, 3H, oxazol. ring —CH₂ and —CH₂CHCO), 4.7 (m, 1H, oxazol. ring —CH), 7.3 (m, 5H, Ar), 9.78 (s, 1H, CHO).

6c. Synthesis of (4S)-4-Benzyl-3-[(2'R)-2'-(tert-butoxy-carbonylmethyl)-(6'RS)-6'-(hydroxy)heptanoyl]-2-oxazolidone The compound of example 6b [1.33 g, 33 mmol] is dissolved in dry)distilled THF and cooled to –15° C. under a N₂ atmosphere. A solution of 3M solution of methyl magnesium bromide in ether [1.1 mL, 33 mmol] is added dropwise with stirring. Stirring is continued for 1 hr. at –15° C., then the reaction is warmed to room temperature and quenched with a aqueous NH₄Cl solution. The THF is evaporated and the reaction is extracted with EtOAc. The combined EtOAc layers are then washed with 5% NaHCO₃, 5% citric acid, and brine, and then dried over Na₂SO₄. Flash chromatography is used to isolate 250 mg of the desired secondary alcohol (18% yield).

¹H- NMR (CDCl₃) : δ1.23 (d, 3H, CHCH₃), 1.4–1.8 (s and m, 16H, t-butyl, —OH, and —(CH₂)₃), 2.55 (dd, 1H, one —COCH₂CHCO), 2.82 (overlapping dd, 2H, one —COCH₂CHCO and one —CHCH₂P), 3.39 (dd, 1H, one —CHCH₂Ph), 3.84 (m, 1H, CHOH, 4.22 (m, 3H, oxazol. ring —CH₂ and —CH₂CHCO), 4.72 (m, 1H, oxazol. ring —CH), 7.3–7.45 (m, 5H, Ar). No peak doubling due to the presence of diasteromers was observed.

6d. Synthesis of (2R)-2-(tert-Butoxycarbonyl)methyl-(6RS)-6-(hydroxy)heptanoic acid The compound of example 6c [0.25 g, 0.6 mmol] is dissolved in 2.5 mL of a 4:1 THF)H₂O solution and cooled to ~2° C., but no lower, under a N₂ atmosphere. Dropwise and with stirring, 30% aqueous H₂O₂, 0.265 mL [0.09 g, 2.6 mmol] is added. After stirring 5 minutes, a solution of LiOH.H₂O [0.042 g, 1.0 mmol] in 1 mL H₂O is added slowly. During these additions, the temperature of the reaction is maintained below 3°–4° C. The temperature of the reaction is slowly allowed to come to room temperature (30 min), and stirred for 1 hr. The reaction is cooled and quenched slowly with Na₂SO₃ [0.126 g, 1.0 mmol] in 2.5 mL H₂O. The THF is evaporated (keeping the temperature low so as not to racemize stereo centers) and the basic, aqueous mixture remaining is extracted with methylene chloride to remove free benzyl oxazolidinone which can be recrystalized and recycled for further use. The basic layer is then cooled and acidified with the slow addition of concentrated HCl (pH 1). The cloudy mixture is then extracted with EtOAc. The EtOAc extracts are dried over Na₂SO₄ and evaporated to give 0.15 g of pure acid (96% yield).

¹H- NMR (CDCl₃) : δ1.25–1.85 (m, 16H, OH, CCH₂CH₂CH₂C, t-butyl H), 2.25–2.68 (two dd, s, COCH₂), 2.73–2.85 (m, 1H, CHCOO), 3.70–3.90 (m, 1H, CHOH).

6e. Synthesis of N-[(2R)-2-(tert-Butoxycarbonylmethyl)-(6RS)-6-hydroxy-heptanoyl]-L-phenylalanine N-methylamide A solution of the compound of example 6d [0.10 g, 0.384 mmol] and L-phenylalanine N-methylamide TFA salt (0.136 g, 0.768 mmol) in dry dimethylformamide (2 mL) under nitrogen is cooled to –6° C. and treated dropwise with diethylcyanophosphonate [0.062 g, 0.384 mmol] followed by triethylamine [0.116 g, 1.15 mmol]. The reaction mixture is stirred at 0° C. for 1 hr, allowed to warm to room temperature over 1 hr, then stirred for two additional hours. The reaction mixture is diluted with water and extracted with ethyl acetate. The combined ethyl acetate layers are sequentially washed with 5% citric acid, saturated sodium bicarbonate, water, and brine. The ethyl acetate is separated, dried (Na₂SO₄), and evaporated. The residue is purified by silica gel column chromatography using 10% methanol in ethyl acetate as the eluent. The appropriate fraction yields 0.15 g (93% yield) of product.

¹H- NMR (CDCl₃) : δ1.14 (d, 3H, —CHCH₃), 1.14–1.7 (m and s, 15H, t-butyl and —(CH₂)₃), 2.27–2.6 (m, 3H, —COCH₂CHCO, —COCH₂CHCO), 2.68 (d, 3H, NCH₃), 3.07 (d, 2H, —CHCH₂Ph), 3.82 (m, 1H, CHOH), 4.68 (q, 1H, NHCHCO), 6.32 (d, 1H, —NHCH₃), 6.63 (d, 1H, —NHCH), 7.24 (m, 5H, Ar). Peak doubling due to diastereomers was observed for —CHCH₃ and —NHCH₃ peaks.

6f. Synthesis of N-[(2R)-2-(Carboxylmethyl-(6RS)-6-(hydroxy)heptanoyl]-L-phenylalanine N-methylamide The compound of example 6e [0.13 g, 0.39 mmol] is dissolved in 7 mL of trifluoroacetic acid (TFA) and 3 mL H₂O and stirred at room temperature until the t-butyl ester is consumed (followed by TLC). The TFA)H₂O is then evaporated and the residue triturated in Et₂O until a white solid is formed. The solid is filtered, washed with fresh Et₂O, and dried in vacuo. 0.05 g of the acid as a white powder is obtained (44% yield).

¹H- NMR (CD₃OD) : δ1.1 (d, 3H, —CHCH₃) 1.15–1.6 (m, 6H, —(CH₂)₃), 2.25 (2 dd, 2H, —CH₂COOH), 2.63 (overlapping m and s, 4H, —COCH₂CHCO and —NCH₃), 2.9 and 3.17 (2 dd, 2H, —CH₂Ph), 3.61 (m, 1H, CHOH), 4.49 (q, 1H, NHCHCO), 7.3 (m, 5H, Ar).

6g.

The compound of example 6f [0.025 g, 0.07 mmol] is dissolved in 5 mL dry)distilled THF and cooled to –15° C. under a N₂ atmosphere. N-methyl morpholine [8.6 µL, 0.077 mmol] is added via syringe with stirring, followed by 10 µL [0.077 mmol] of isobutylchloroformate. The solution becames slightly cloudy. The reaction is stirred for 30 min. at –15° C., then 17 µL [0.14 mmol] of O-trimethylsilyl hydroxyl amine is added. After stirring for 1.5 hrs. the reaction is poured onto 5 mL of 5% NaHCO₃ then extracted with EtOAc. The organic layer is separated and washed with 5% citric acid, H₂O, and brine, then dried over Na₂SO₄. The solvent is evaporated to give 0.01 g of hydroxamate (37% yield).

¹H- NMR (CD₃OD) : δ1.1 (d, 3H, —CHCH₃), 1.15–1.6 (m, 6H, —(CH₂)₃), 2.15 (2 dd, 2H, —CH₂COOH), 2.63 (overlapping m and s, 4H, —COCH₂CHCO and NCH₃), 2.9 and 3.17 (2 dd, 2H, —CH₂Ph), 3.61 (m, 1H, CHOH), 4.49 (q, 1H, NHCHCO), 7.3 (m, 5H, Ar).

EXAMPLE 7

Alternative route to N-[(2R)-2-(tert-Butoxycarbonylmethyl)-(6RS)-6-hydroxy-heptanoyl]-L-phenylalanine N-methylamide 7a. Synthesis of N-[(2R)-2-(tert-Butyoxycarbonylmethyl)-6-(hydroxy)hexanoyl]-L-phenylalanine N-methylamide The compound obtained in example 1g [2.0 g, 4 mmol] in 20 mL absolute EtOH is treated with 0.75 g 20% Pd(OH)₂/C and 3.8 mL [40 mmol] of 1,4-cyclohexadiene. The reaction is heated slowly to 65° C. and stirred as such for ~20 hrs. The reaction is cooled and filtered through Celite. The Celite is washed with EtOAc, and the combined filtrates evaporated. The residue is flash chromatographed, resulting in a white solid [1.14 g, 70% yield].

¹H- NMR (CDCl₃) : δ1.3–1.7 (m and s, 15H, t-butyl and —CH₂)₃), 2.35–2.8 (m, 3H, —COCH₂CHCO and —COCH₂CHCO), 2.74 (d, 3H, NCH₃), 3.14 (2 d, 2H, —CHCH₂Ph), 3.64 (m, 2H, —CH₂OH), 4.62 (q, 1H, NHCHCO), 6.35 (d, 1H, —NHCH₃), 6.71 (d, 1H, —NHCH), 7.3 (m, 5H, Ar).

7b. Synthesis of N-[(2R)-2-(tert-Butoxycarbonylmethyl)-5-(formyl)pentanoyl]-L-phenylalanine N-methylamide The compound of example 7a [0.05 g, 0.12 mmol] and 0.06 g, [0.24 mmol] of pyridinium chlorochromate (PCC) are dissolved in 10 mL of anhydrous CH₂Cl₂ under a N₂ atmosphere and stirred at room temperature. The reaction is followed by TLC until the alcohol is consumed. EtOAc is then added to precipitate PCC salts, and the reaction is filtered through Celite several times. The solvent is evaporated and the residue flash chromatographed to afford 0.07 g (47%) of the aldehyde as a gummy solid.

¹H- NMR (CDCl₃) : δ1.4–1.75 (m and s, 13H, t-butyl and —CH₂)₂), 2.4–2.75 (m, 5H, —COCH₂CHCO, —COCH₂CHCO, —CH₂CHO), 2.8 (d, 3H, NCH₃), 3.2 (2 dd, 2H, —CHCH₂Ph), 4.66 (q, 1H, NHCHCO), 6.18 (d, 1H, —NHCH₃), 6.63 (d, 1H, —NHCH), 7.3 (m, 5H, Ar) 9.8 (s, 1H, CHO).

7c. Synthesis of N-[(2R)-2-(tert-Butoxycarbonylmethyl)-(6RS)-6-hydroxy-heptanoyl]-L-phenylalanine N-methylamide Titanium isopropoxide [0.211 g, 0.74 mmol] is dissolved in 5 mL dry/distilled THF and cooled to –10° C. under a N₂ atmosphere. A solution of 1.0M titanium (IV) chloride in CH₂Cl₂ [0.25 mL, 0.25 mmol] is then added dropwise via syringe. The reaction is then warmed to room temperature and stirred 1.5 hours. The reaction is cooled to –78° C. and 0.71 mL [0.98 mmol] of 1.4M methyl lithium in Et₂O is added via syringe. The reaction becomes red in color, and upon warming slowly to room temperature, lithium chloride (LiCl) precipitates from the reaction, causing it to also be cloudy. After 1 hour, stirring is stopped and the LiCl is allowed to settle. The solution of triisopropoxymethyl titanium is again cooled to –78° C. then transferred slowly via syringe to a dry/distilled THF solution (7 mL) of 0.1 g [0.25 mmol] of the compound formed in example 7b cooled to –78° C. under a N₂ atmosphere. The reaction is warmed slowly to 0° C., stirred for 1 hour, then quenched with dilute aqueous HCl. The THF is evaporated and the aqueous layer extracted with EtOAc. The organic layer is washed with H₂O and brine, and then dried over Na₂SO₄. Flash chromatography is used to isolate 0.01 g of the desired secondary alcohol (10% yield).

¹H- NMR (CDCl₃) : δ1.14 (d, 3H, —CHCH₃), 1.14–1.7 (m and s, 15H, t-butyl and —(CH₂)₃), 2.27–2.6 (m, 3H, —COCH₂CHCO, —COCH₂CHCO), 2.68 (d, 3H, NCH₃), 3.07 (d, 2H, —CHCH₂Ph), 3.82 (m, 1H, CHOH), 4.68 (q, 1H, NHCHCO), 6.32 (d, 1H, —NHCH₃), 6.63 (d, 1H, —NHCH), 7.24 (m, 5H, Ar). Peak doubling due to diastereomers was observed for —CHCH₃ and —NHCH peaks.

EXAMPLE 8

(2S)-N-2-[(2'R)-2'-[2"-(Hydroxyamino)-2"-(oxo)ethyl]-6'-(phenylmethoxy)hexanoyl]amino-3,3-dimethylbutanoic acid N-methylamide 8a. Synthesis of (2S)-N-2-[(2'R)-2'-(tert-Butoxycarbonylmethyl)-6'-(phenylmethoxy)hexanoyl]amino-3,3-dimethylbutanoic acid N-methylamide A stirred solution of the compound of example 1f (0.3 g, 0.9 mmol) and (2S)-2-Amino-3,3-dimethylbutanoic acid N-methyl amide hydrochloride (0.187 g, 1 mmol) in 3 mL DMF under nitrogen is cooled to –5° C., and is treated with diethylcyanophosphonate (0.19 mL, 1.2 mmol), followed by dropwise addition of triethylamine (0.4 mL, 2.8 mmol). The reaction mixture is stirred cold for 2.5 hours, then at ambient temperature for 2.5 hours longer. The reaction mixture is then diluted with 30 mL of ethyl acetate, and washed sequentially with 5% citric acid solution, 5% sodium bicarbonate solution, and brine. The ethyl acetate is separated, dried over anhydrous sodium sulfate, filtered, and evaporated to 424 mg (91%) of a colorless oil, which can be used in the following step without further purification.

¹H NMR (CDCL₃) : δ1.00 (s, 9H, (CH₃)₃), 1.2–1.75 (m, 15H), 2.30–2.70 (m, 3H, COCH₂CHCO), 2.80 (D, 2H, NHCH₃), 3.45 (t, 2H, CH₂O), 4.25 (d, 1H, NCHCO), 4.50 (s, 2H, PhCH₂O), 6.15 (bs, 1H, NH), 6.55 (d, 1H, NH), 7.2–7.5 (m, 5H, Ar).

8b. Synthesis of (2S)-N-2-[(2'R)-2'-(carboxymethyl)-6'-(phenylmethoxy)hexanoyl]amino-3,3-dimethylbutanoic acid N-methylamide The compound of example 8a (424 mg, 0.9 mmol) is dissolved in a mixture of trifluoroacetic acid (3 mL) and water (1 mL), and stirred at ambient temperature for 3 hours. The solvents are evaporated, and the residue placed under high vacuum for 2 hours. The oily residue is purified by flash silica gel chromatography (2% methanol in CH₂Cl₂). Product containing fractions is evaporated to yield 295 mg (81%) of a white foam.

¹H NMR (CDCL₃) : δ0.95 (s, 9H, (CH₃)₃), 1.20–1.70 (m, 6H), 2.40–2.75 (m, 3H, COCH₂CHCO), 2.80 (d, 2H, NCH₃), 3.40 (t, 2H, CH₂), 4.40 (d, 1H, NCHCO), 4.50 (s, 2H ArCH₂O), 6.70 (bs, 1H, NH), 7.23–7.6 (m, 6H, Ar & NH).

8c.

To a –10° C. stirred solution of the compound of example 8b (295 mg, 0.73 mmol) in 3 mL of dry distilled THF under nitrogen is added in one portion N-methylmorpholine (0.09 mL, 0.8 mmol). After stirring 5 minutes, the reaction mixture is treated dropwise with isobutylchloroformate (0.1 mL, 0.8 mmol), and the resultant suspension is stirred for 15 to 20 minutes. The reaction mixture is then treated with O-(trimethysilyl)hydroxylamine (84 mg, 0.8 mmol), and the stirring continued for 2 hours at ice bath temperature, followed by 2 hours at ambient temperature. The reaction mixture is filtered, and the filtrate evaporated to a white foam. The foam is stirred overnight in 10 mL of diethyl ether, which produces the desired hydroxamate as a white solid (220 mg, 71%).

¹H NMR (DMSO d₆) : δ0.90 (s, 9H, (CH₃)₃), 1.10–1.60 (m, 6H), 1.95–2.20 (m, 2H), 2.50 (d, 3H, NCH₃), 2.79 (m, 1H), 4.15 (d, 1H, COCHN), 4.40 (s, 2H, ArCH₂O), 7.20–7.40 (m, 5H, Ar), 7.67 (d, 1H, NH), 7.85 (bs, 1H, NH), 8.65 (s, 1H, OH).

EXAMPLE 9

(2S)-N-2-[(2'R)-2'-[2"-(Hydroxyamino)-2"-(oxo)ethyl]-6'-(hydroxy)hexanoyl]amino-3,3-dimethylbutanoic acid N-methylamide 9a. Synthesis of (2S)-N-2-[(2'R)-2'-(tert-Butoxycarbonylmethyl)-6'-(hydroxy)hexanoyl]-amino-3,3-dimethylbutanoic acid N-methylamide Under a nitrogen atmosphere, a solution of the compound formed in example 8a (1.5 g, 3.2 mmol) in ethanol (25 mL) is treated with 20% Pd(OH)₂ on C (0.6 g) and 1,4-cyclohexadiene (10 mL). The mixture is heated at 65° C. for 16 hours at which point 0.5 g of 20% Pd(OH)₂ on C and 1,4-cyclohexadiene (4 mL) is added and heating is continued for another 5 hours. The reaction mixture is cooled and the catalyst is collected via filtration. The filtrate is evaporated to dryness and the residue is purified by silica gel column chromatography using 5% methanol in ethyl acetate as the eluent to give the desired product (0.85 g, 71% yield).

¹H NMR (CDCl₃) δ0.95 (s, 9H, t-butyl H), 1.15–1.80 (m, 15H, CCH₂CH₂CH₂C and t-butyl H), 2.40 (dd, 1H, COCH₂CHCO), 2.50–2.90 (m, 5H, NCH₃, COCH₂CHCO), 3.45–3.75 (m, CH₂O), 4.40 (d, 1H, NCH), 6.70 (m, 1H, NH), 7.26 (m, 1H, NH).

9b. Synthesis of (2S)-N-2_[(2'R)-2'-(Carbonylmethyl)-6'-(hydroxy)hexanoyl]amino-3,3-dimethylbutanoic acid N-methylamide The compound of example 9a (0.6 g, 1.6 mmol) is dissolved in 10 mL of a 7:3 trifluoroacetic acid-water mixture and stirred at room temperature for 4.0 hours. The solvents are removed on a rotary evaporator and the residue is treated with acetonitrile and evaporated (three times) in order to azeotrope water. The colorless gummy product (0.635 g) is dried on a high vacuum pump. The product does not solidify, perhaps due to remaining impurities and trifluoroaetic acid. The compound without any further purification is used in next reaction.

$^1$H NMR (MeOH-d$_4$) δ0.95 (s, 9H, t-butyl H), 1.20–1.85 (m, 6H, CCH$_2$CH$_2$CH$_2$C), 2.35–3.00 (m, 6H, NCH$_3$, COCH$_2$CHCO), 3.64 (m, 2H, CH$_2$O), 4.45 (d, 1H, NCH).

9c.

Under a nitrogen atmosphere, the compound of example 9b (0.143 g, 0.4 mmol), dissolved in dry tetrahydrofuran (10 mL), is cooled to −15° C. and treated with N-methylmorpholine (0.081 g, 0.8 mmol). After 5 min, isobutylchloroformate (0.109 g, 0.8 mmol) is added dropwise and the reaction mixture is stirred for 15 min. O-(trimethylsilyl)hydroxylamine (0.25 g, 2.4 mmol) is added dropwise. The reaction mixture is stirred at −15° C. for 1 hour, followed by 1 hour at 0° C., then 30 minutes at room temperature. The reaction mixture is filtered and the filtrate is evaporated to dryness. The crude product is purified by preparative thin layer chromatography using 25% methanol in ethyl acetate as eluent, giving a colorless solid product (0.068 g, 45% yield).

$^1$H NMR (MeOH-d$_4$) δ0.77 (s, 9H, t-butyl H), 0.90–1.50 (m, 6H, CCH$_2$CH$_2$CH$_2$C), 1.90–2.25 (two dd's, 2H, CH$_2$CO), 2.50 (s, 3H, NCH$_3$), 2.56–2.78 (m, 1H, CHCO), 3.30 (t, 2H, CH$_2$O), 3.98 (s, 1H, NCH).

EXAMPLE 10

N-[(2R)-2-[2'-(Hydroxyamino)-2'-(oxo)ethyl]-5-(phenylmethoxy)pentanoyl]-L-phenylalanine N-methylamide Synthesis using a procedure analogous to that of Example 2 results in a compound having the following analysis:

$^1$H-NMR (CD$_3$OD) : δ1.24–1.36 (m, 4H, —(CH$_2$)$_2$), 1.95 (2 dd, 2H, —CH$_2$CONHOH), 2.5 (overlapping s and m, 4H, —NCH$_3$ and —CHCH$_2$CONHOH), 2.75 and 2.98 (2 dd, 2H, —CCH$_2$Ph), 3.27 (t, 2H, —CH$_2$OCH$_2$Ph), 4.33 (overlapping s and q, 3H, —OCH$_2$Ph and —NCHCO), 7.06–7.33 (m, 10H, Ar).

EXAMPLE 11

N-[(2R)-2-[2'-(Hydroxyamino)-2'-(oxo)ethyl]-7-(phenylmethoxy)heptanoyl]-L-phenylalanine N-methylamide)

Synthesis using a procedure analogous to Example 2 results in a compound which is produces the following analysis:

$^1$H-NMR (CD$_3$OD) : δ1.01–1.5 (m, 8H, —(CH$_2$)$_4$), 1.98–2.21 (2 dd, 2H, —CH$_2$CONHOH), 2.52 (m, 1H, —CHCH$_2$CONHOH), 2.59 (s, 3H, —NCH$_3$), 2.86 and 3.09 (2 dd, 2H, —CHCH$_2$Ph), 3.38 (t, 2H, —CH$_2$OCH$_2$Ph), 4.41 (overlapping s and q, 3H, —OCH$_2$Ph and —NCHCO), 7.05–7.28 (m, 10H, Ar).

EXAMPLE 12

N-[(2'R)-2-[2'-(Hydroxyamino)-2'-(oxo)ethyl]-6-(4'-oxobutylamino)hexanoyl]-L-phenylalanine N-methylamide 12a. Synthesis of (4S)-4-Benzyl-3-[(2'R)-2'-(tert-butoxycarbonylmethyl)-6'-(methanesulfonyloxy)hexanoyl]-2-oxazolidone 0.5 g [1.23 mmol] of the product formed in example 6a, 0.24 mL [1.72 mmol] of Et$_3$N, and 0.03 g of 4-dimethylamino pyridine [0.246 mmol] are dissolved in 10 mL dry CH$_2$Cl$_2$ and cooled to 0° C. under N$_2$. Methanesulfonyl chloride [0.105 mL, 1.35 mmol] is then added dropwise via syringe with stirring. The reaction is stirred at 0° C. for 2 hrs. then warmed to room temperature and quenched with H$_2$O. The layers were separated and the organic layer was washed with 5% NaHCO$_3$, 5% citric acid, H$_2$O, and brine, then dried over Na$_2$SO$_4$. Evaporation of the solvent affords 0.5 g of the desired product (96%) as a colorless oil. No further purification is done.

$^1$H NMR (CDCl$_3$) : δ1.41–1.84 (m and s, 15H, -t-Bu and —(CH$_2$)$_3$), 2.48 (dd, 1H, —CH$_2$COOtBu), 2.84 (2 overlapping dd, 2H, one —CH$_2$COOtBu and one —CHCH$_2$Ph, 3.02 (s, 3H, —SO$_2$CH$_3$), 3.34 (dd, 1H, —CHCH$_2$Ph), 4.13–4.28 (m, 5H, —CH$_2$OSO$_2$, oxazol. ring —CH$_2$, and —CHCH$_2$COOtBu), 4.69 (m, 1H, oxazol. ring —CH), 7.23–7.39 (m, 5H, Ar).

12b. Synthesis of (4S)-4-Benzyl-3-[(2'R)-2'-(tert-butoxycarbonylmethyl)-6'-(azido)-hexanoyl]-2-oxazolidone The compound of example 12a [2.1 g, 4.34 mmol] and tetrabutylammonium iodide [1.6 g, 4.34 mmol] are dissolved in 20 mL toluene. A sodium azide solution [2.8 g, 43 mmol] in 20 mL H$_2$O is then added and the two-phase reaction stirred vigorously at 70° C. for 17 hours under N$_2$. The reaction is cooled, the layers separated, and the aqueous layer extracted with EtOAc. The EtOAc and toluene layers are combined and washed with 5% NaHCO$_3$, 5% citric acid. H$_2$O, and brine, then dried over Na$_2$SO$_4$. The solvent is evaporated, leaving an oil residue which solidifies. The solid is recrystallized from Et$_2$O/hexane which yields 1.5 g of the desired azide (80%) as white crystals.

$^1$H-NMR (CDCl$_3$) : δ1.45–1.75 (m and s, 15H, -t-Bu and —(CH$_2$)$_3$), 2.47 (dd, 1H, —CH$_2$COOtBu), 2.78 (2 overlapping dd, 2H, one —CH$_2$COOtBu and one —CHCH$_2$Ph), 3.28 (t, 2H, —CH$_2$N$_3$), 3.34 (dd, 1H, —CHCH$_2$Ph), 4.17 (m, 3H, oxazol. ring —CH$_2$, and —CHCH$_2$COOtBu), 4.67 (m, 1H, oxazol. ring —CH), 7.23–7.37 (m, 5H, Ar).

12c. Synthesis of (2R)-2-(tert-Butoxycarbonylmethyl)-6-(azido)hexanoic acid

The compound of example 12c [0.3 g, 0.7 mmol] is dissolved in 15 mL of a 4:1 THF/H$_2$O solution and cooled to −2° C., but not below, under a N$_2$ atmosphere. A solution of 30% aqueous H$_2$O$_2$ [0.285 mL, 2.8 mmol] is then added via syringe while maintaining the temperature below 5° C. After stirring 5 minutes, a solution of LiOH.H$_2$O [0.046 g, 1.12 mmol] in 2 mL H$_2$O is added slowly via syringe. Some gas evolution is observed. The reaction is stirred for 10 minutes, then warmed to room temperature and stirred 1 hour. A solution of Na$_2$SO$_3$ [0.35 g, 2.8 mmol] in 2mL H$_2$O is then added dropwise; some heat is evolved during this process, so the reaction is cooled. After stirring ~20 minutes, the THF is evaporated (below 30° C.) and the remaining basic layer is extracted with EtOAc. These EtOAc extracts contain free (S)-(−)-4-benzyl-2-oxazolidone which is recrystalized and recycled for further use. The basic layer is cooled and acidified with the slow addition of concentrated aqueous HCl to a pH 2–3. The cloudy mixture is extracted with EtOAc, and the EtOAc dried over Na$_2$SO$_4$ and evaporated to give 0.17 g of pure acid (90% yield).

$^1$H-NMR (CDCl$_3$) : δ1.39–1.7 (m and s, 15H, -t-Bu and —(CH$_2$)$_3$), 2.4 (dd, 1H, —CH$_2$COOtBu), 2.65 (dd, 2H, —CH$_2$COOtBu), 2.82 (m, 1H, —CHCH$_2$COOtBu), 3.29 (t, 2H, —CH$_2$N$_3$).

12d. Synthesis of N-[(2R)-2-(tert-Butoxycarbonylmethyl)-6-(azido)hexanoyl]-L-phenylalanine N-methylamide The compound of example 12c [0.17 g, 0.64 mmol] and L-phenylalanine methyl amide TFA salt [0.182 g, 0.7 mmol]

are dissolved in 10 mL dry DMF and cooled to –10° C. under a $N_2$ atmosphere. Diethylcyanophosphonate [0.101 mL, 0.67 mmol], followed by $Et_3N$ [0.264 mL, 1.9 mmol], are added dropwise via syringe. The reaction is stirred for 1 hour at –10° C. then at room temperature for 2 hours. The reaction is diluted with 30 mL $H_2O$ and extracted with EtOAc. The combined EtOAc layers are then washed with 5% $NaHCO_3$, 5% citric acid, $H_2O$, and brine, then dried over $Na_2SO_4$. The solvent is evaporated, and the residue flash chromatographed, affording 1.05 g of the coupled product (74% yield).

$^1$H-NMR (CDCl$_3$) : δ1.4–1.68 (m and s, 15H, -t-Bu and —(CH$_2$)$_3$), 2.3–2.58 (m, 3H, —CHCH$_2$CootBu), 2.7 (d, 3H, —NCH$_3$), 3.09 (2 dd, 2H, —CHCH$_2$Ph), 3.21 (t, 2H, —CH$_2$N$_3$) 4.51 (q, 1H, NCHCO), 5.81 (d, 1H, —NH), 6.35 (d, 1H, NH), 7.19–7.33 (m, 5H, Ar).

12e. Synthesis of N-[(2R)-2-(tert-Butoxycarbonylmethyl)-6-(amino)hexanoyl]-L-phenylalanine N-methylamide The compound of example 12d [0.083 g 0.19 mmol] in 15 mL dry/distilled THF is hydrogenated (0.1 g 10% Pd/C, 30 psi, 25° C., 1.2 hours.) on a Parr shaker apparatus. After this time, the reaction is filtered through Celite and the Celite washed with EtOH. The combined filtrates are evaporated, leaving 0.084 g of a gummy solid. No further purification is done (>90% yield).

$^1$H-NMR (CD$_3$OD) : δ1.1–1.5 (m and s, 15H, -t-Bu and —(CH$_2$)$_3$), 2.15–2.41 (m, 3H, —CHCH$_2$COOtBu), 2.47–2.61 (overlapping s and t, 5H, —CH$_2$NH$_2$ and —NCH$_3$), 2.9 and 3.05 (2 dd, 2H, —CHCH$_2$Ph), 4.41 (t, 1H, —NCHCO), 7.07–7.26 (m, 5H, Ar).

12f. Synthesis of N-[(2R)-2-(tert-Butoxycarbonylmethyl)-6-(4'-oxobutylamino)-hexanoyl]-L-phenylalanine N-methylamide The compound of example 12e [0.394 g, 0.97 mmol] is dissolved in 15 mL dry DMF and cooled to –10° C. under a $N_2$ atmosphere. Triethylamine [0.203 mL, 1.46 mmol], followed by butyroyl chloride [0.111 mL, 1.07 mmol] are added dropwise via syringe. The reaction becomes slightly cloudy white. The reaction is stirred 20 minutes at –10° C. then warmed to room temperature and stirred 1.5 hours. The reaction mixture was treated with 40 mL $H_2O$ and then extracted with EtOAc. The combined extracts were washed with 5% $NaHCO_3$, 5% citric acid, $H_2O$, and brine, then dried over $Na_2SO_4$. The solvent is evaporated, leaving a fluffy white solid which is recrystalized from $CH_3CN/Et_2O$ and washed with cold $Et_2O$. This affords 0.29 g of the desired acyl amine (63% yield).

$^1$H-NMR (CDCl$_3$) : δ0.95 (t, 3H, —CH$_2$CH$_3$), 1.2–1.71 (m and s, 17H, -t-Bu and —(CH$_2$)$_4$), 2.15 (t, 2H, —NCOCH$_2$), 2.27–2.59 (m, 3H, —CHCH$_2$COOtBu), 2.7 (d, 3H, —NCH$_3$), 3.09 (2 dd, 2H, —CHCH$_2$Ph), 3.21 (m, 2H, —CH$_2$NH), 4.51 (q, 1H, —NCHCO), 5.81 (broad s, 1H, —NH), 5.89 (broad s, 1H, —NH), 6.35 (d, 1H, —NH), 7.14–7.34 (m, 5H, Ar).

12g. Synthesis of N-[(2R)-2-(Carboxymethyl)-6-(4'-oxobutylamino)hexanoyl]-L-phenylalanine N-methylamide The compound of example 12f [0.15 g, 0.31 mmol] was dissolved in 10 mL of a 7:3 TFA/$H_2O$ solution and stirred at room temperature until the t-butyl ester is consumed (followed by TLCV). The TFA/$H_2O$ is then evaporated, and the residue triturated in $Et_2O$, producing a white solid. The solid is filtered, washed with $CH_3CN$ several times, and dried in vacuo. 0.125 g of the acid as a white powder are obtained (94% yield).

$^1$H-NMR (CD$_3$OD) : δ0.87 (t, 3H, —CH$_2$CH$_3$), 1.02–1.63 (m, 8H, —(CH$_2$)$_4$), 2.08 (t, 2H, —NCOCH$_2$), 2.2–2.48 (2 dd, 2H, —CH$_2$COOH), 2.56 (overlapping s and m, 4H, —NCH$_3$ and —CHCH$_2$COOH), 2.84–3.1 (overlapping t and 2 dd, 4H, —CH$_2$NH and —CHCH$_2$Ph), 4.41 (t, 1H, NCHCO), 7.02–7.27 (m, 5H, Ar).

12h.

The compound of example 12g [0.08 g, 0.19 mmol] is dissolved in ~5 mL dry DMF and cooled to –10° C. under a $N_2$ atmosphere. The reaction mixture is treated with N-methylmorpholine [0.026 mL, 0.23 mmol], followed by isobutylchloroformate [0.030 mL, 0.23 mmol] via syringe with stirring. The solution becomes slightly cloudy. The reaction is stirred for 30 min. at –10° C., then 0.058 mL [0.48 mmol] of O-trimethylsilyl hydroxylamine is added via syringe and stirred another 1.5 hours at –10° C. The reaction is warmed to room temperature and the solvent evaporated. The gummy residue is triturated in $Et_2O$, causing it to solidify. The solid is triturated ($CH_3CN$) and recrystalized (MeOH/$CH_3CN$) several times to give 0.065 g of hydroxamate as a white powder (78% yield).

$^1$H-NMR (CD$_3$OD) : δ0.85 (t, 2H, —CH$_2$CH$_3$), 0.99–1.61 (m, 8H, —(CH$_2$)$_4$), 1.98 –2.2 (overlapping t and 2 dd, 4H, —CH$_2$NHCOCH$_2$ and —CH$_2$CONHOH), 2.48–2.63 (overlapping s and m, 4H, —CHCH$_2$CONHOH and —NCH$_3$), 2.81–3.11 (overlapping t and 2 dd, 4H, —CH$_2$NH and —CHCH$_2$Ph), 4.41 (q, 1H, NCHCO), 7.13–7.25 (m, 5H, Ar).

EXAMPLE 13

N-[(2R)-2-[2'-(Hydroxyamino)-2'-(oxo)ethyl]-6-(phenoxy)-hexanoyl]-L-phenylalanine N-methylamide 13a. Synthesis of N-[(2R)-2-(tert-butoxycarbonylmethyl)-6-(phenoxy)hexanoyl]-L-phenylalanine N-methylamide Diethyl azodicarboxylate [DEAD] (0.145 g, 0.837 mmol) is added to a solution of triphenylphosphine (0.218 g, 0.837 mmol) in 20 mL of dry THF under a nitrogen atmosphere. The mixture is stirred at room temperature for 15 minutes. Phenol (0.078 g, 0.837 mmol), followed by the compound of example 3a (0.340 g, 0.837 mmol), is added and the resulting mixture stirred at room temperature for 18 hours. The solvent is evaporated to dryness and the residue is partitioned between water and methylene chloride. The methylene chloride layer is washed with water and brine, then purified by preparative thin-layer chromatography using 60% ethyl acetate in hexanes as eluent (0.255 g, 63.2% yield).

$^1$H NMR (CDCl$_3$) δ1.25–1.85 (m, 15H, CCH$_2$CH$_2$CH$_2$C and t-butyl H), 2.28–2.78 (m, 6H, NCH$_3$, CH$_2$CO and CHCO), 3.00–3.20 (m, 2H, OCH$_2$Ph), 3.88 (t, 2H, OCH$_2$C), 4.54 (dd, 1H, NCH), 5.95 (m, 1H, NH), 6.45 (,d, 1H, NH), 6.75–7.40 (m, 10H, ArH).

13b. Synthesis of N[(2R)-2-(carboxymethyl)-6-(phenoxy)hexanoyl]-L-phenylalanine N-methylamide A solution of the compound of example 13a (0.213 g, 0.442 mmol) in trifluoroacetic acid (4 mL) and methylene chloride (6mL) is stirred at room temperature for 5 hours. The solvents are removed on a rotary evaporator. The residue is placed on a high vacuum pump for 2 hours, then triturated with diethyl ether and hexanes to produce a colorless solid. The solid was collected by filtration and air dried (0.165 g, 87.7% yield).

$^1$H NMR (CD$_3$OD) δ1.00–1.60 (m, 6H, CCH$_2$CH$_2$CH$_2$C), 2.05–2.60 (m, 6H, NCH3, CH2CO and CHCO), 2.69–3.00 (two dd, 2H, CCH2Ph), 3.66 (t, 2H, OCH2C), 4.30 (dd, 1H, NCH), 6.60–7.20 (m, 10H, ArH).

13c.

Under a nitrogen atmosphere, the compound of example 13b (0.106 g, 0.25 mmol) is dissolved in dry THF (10 mL), and treated with N-methylmorpholine (0.076 g, 0.75 mmol) via syringe. The reaction mixture is cooled to −15° C. and treated with isobutylchloroformate (0.05 mL, 0.37 mmol) via syringe. After stirring the suspension for 15 minutes, O-(trimethylsilyl)hydroxylamine (0.105 mL, 1 mmol) is added and the reaction mixture is stirred at −15° C. for 1 hour, followed by 1 hour at 0° C., then 30 minutes at room temperature. The reaction mixture is filtered and the filtrate is evaporated to dryness. The crude product is purified by preparative thin-layer chromatography using 15% methanol in ethyl acetate as eluent (0.0634 g, 57.4% yield).

$^1$H NMR (CD$_3$OD) δ0.90–1.60 (m, 6H, CCH$_2$CH$_2$CH$_2$C), 1.80–2.14 (two dd, 2H, CH$_2$CO), 2.32–2.54 (m, 4H, NCH$_3$, CHCO) 2.54 (dd) and 2.94 (dd) (2H CH$_2$Ph), 3.68 (t, 2H, OCH$_2$), 4.32 (dd, 1H, NCH), 6.6–7.7 (m, 10H, ArH).

EXAMPLE 14

N-[(2R)-2-[2'-(Hydroxyamino)-2'-(oxo)ethyl]-7-(phenoxy)-heptanoyl]-L-phenylalanine N-methylamide Synthesis using a procedure analogous to that of example 13 results in a compound having the following analysis.

$^1$H NMR (CD$_3$OD) δ0.8–1.60 (m, 8H, CCH$_2$CH$_2$CH$_2$C), 1.84–2.10 (m, 2H, CH$_2$CO), 2.40–2.60 (m, 4H, NCH$_3$, CHCO), 2.72 (dd) and 2.94 (dd) (2H, CH$_2$Ph), 3.72 (t, 2H, OCH$_2$), 4.30 (dd, 1H, CNH), 6.59–6.75 (m, 2H, ArH), 6.90–7.20 (m, 8H, ArH).

EXAMPLE 15

(2S)-N-2'-[(2'R)-2'-[2"-(Hydroxyamino)-2"-(oxo)ethyl]-6'-(2-phenethylamino)-6' (oxo)hexanoyl]amino-3,3-dimethylbutanoic acid N-methylamide Synthesis using a procedure analogous to that of example 5 results in a compound having the following analysis.

$^1$H NMR (CD$_3$OD) ε0.98 (s, 9H, t-butyl H), 1.30–1.7 (m, 6H), 2.10 (t, 2H, CH$_2$CO), 2.38 (dd, 1H), 2.50–2.65 (m, 2H), 2.76 (s, 3H, NCH$_3$), 2.80 (t, 2H, NHCH$_2$), 3.40 (t, 2H, CH$_2$Ph), 4.20 (d, 1H, NCH), 7.10–7.30 (m, 5H, ArH), 7.80 (d, 1H, NH).

EXAMPLE 16

(2S)-N-2'-[(2'R)-2'-[2"-(Hydroxyamino)-2"-(oxo)ethyl]-6'-(4-methylphenoxy)hexanoyl]amino-3,3-dimethylbutanoic acid N-methylamide Synthesis using a procedure analogous to that of example 13 results in a compound having the following analysis.

$^1$H NMR (CD$_3$OD) δ0.91 (s, 9H, t-butyl), 1.28–1.7 (m, 6H, (CH$_2$)$_3$), 2.1–2.32 (overlapping s and dd, 5H, PhCH$_3$ and CH$_2$CONHOH), 2.61 (s, 3H, NCH$_3$), 2.8 (m, 1H, CHCH$_2$CONHOH), 3.81 (t, 2H, CH$_2$OPh), 4.12 (d, 1H, NCH), 6.69 (d, 2H, ArH), 6.97 (d, 2H, ArH).

EXAMPLE 17

(2S)-N-2'-[(2'R)-2'-[2"-(Hydroxyamino)-2"-(oxo)ethyl]-6'-(4-chlorophenoxy)hexanoyl]amino-3,3-dimethylbutanoic acid N-methylamide Synthesis using a procedure analogous to that of example 13 results in a compound having the following analysis.

$^1$H NMR (CD$_3$OD) δ0.91 (s, 9H, t-butyl), 1.25–1.74 (m, 6H, (CH$_2$)$_3$), 2.1–2.32 (dd, 2H, CH$_2$CONHOH), 2.59 (s, 3H, NCH$_3$), 2.8 (m, 1H, CHCH$_2$CONHOH), 3.83 (t, 2H, CH$_2$OPh), 4.12 (d, 1H, NCH), 6.78 (d, 2H, ArH), 7.13 (d, 2H, ArH)

EXAMPLE 18

(2S)-N-2'-[(2'R)-2'-[2"-(Hydroxyamino)-2"-(oxo)ethyl]-6'-(3-methylphenoxy)hexanoyl]amino-3,3-dimethylbutanoic acid N-methylamide Synthesis using a procedure analogous to that of example 13 results in a compound having the following analysis.

$^1$H NMR (CD$_3$OD) δ0.98 (s, 9H, t-butyl), 1.32–1.77 (m, 6H, (CH$_2$)$_3$), 2.16–2.4 (overlapping s and dd, 5H, PhCH$_3$ and CH$_2$CONHOH), 2.65 (s, 3H, NCH$_3$), 2.85 (m, 1H, CHCH$_2$CONHOH), 3.85 (t, 2H, CH$_2$OPh), 4.2 (d, 1H, NCH), 6.6 (overlapping t and s, 3H, ArH), 7.09 (t, 1H, ArH)

EXAMPLE 19

(2S)-N-2'-[(2'R)-2'-(carboxymethyl)-6'-(3-methylphenoxy)hexanoyl]amino-3,3-dimethylbutanoic acid N-methylamide Synthesis using a procedure analogous to that of example 13 results in a compound having the following analysis.

$^1$H NMR (CD$_3$OD) δ0.97 (s, 9H, t-butyl), 1.36–1.8 (m, 6H, (CH$_2$)$_3$), 2.25 (s, 3H, PhCH$_3$), 2.4–2.59 (dd, 2H, CH$_2$COOH), 2.64 (s, 3H, NCH$_3$), 2.84 (m, 1H, CHCH$_2$CONHOH), 3.9 (t, 2H, CH$_2$OPh), 4.2 (d, 1H, NCH), 6.68 (overlapping t and s, 3H, ArH), 7.09 (t, 1H, ArH)

The potency of compounds of the present invention to act as inhibitors of the MMPs is determined by using recombinant MMPs as follows.

Human cDNA for fibroblast collagenase and fibroblast stromelysin is obtained (Goldberg, G. I., Wilhelm, S. M., Kronberger, A., Bauer, E. A., Grant, G. A., and Eisen, A. Z. (1986) J. Biol. CHem. 262, 5886–9). Human cDNA for neutrophil collagenase is obtained (Devarajan P., Mookhtiar, K., Van Wart, H. E. and Berliner, N. (1991) Blood 77, 2731–2738). The MMPs are expressed in E. coli as inclusion bodies with the expression vector pET11a (Studier, F. W., Rosenberg, A. H. Dunn, J. J., and Dubendorff, J. W. (1990) Methods in Enzymology 185, 60–89). Fibroblast stromelysin and neutrophil collagenase are expressed as mature enzymes with C-terminal truncations, Phe83-Thr260 and Met100-Gly262, respectively. Fibroblast collagenase is expressed as a proenzyme with a C-terminal truncation, Met1-Pro250. Inclusion bodies are solubilized in 6M urea, purified by ion exchange, and folded into their native conformation by removal of urea. Fibroblast collagenase is activated by incubation with p-aminophenylmercury. All active MMPs are purified by gel filtration.

MMPs are assayed with peptide substrates based on R-Pro-Leu-Ala-Leu-X-NH-R$_2$, where R=H or benzoyl, X=Trp or O-methyl-Tyr, R$_2$=Me or butyldimethylamino. The product is determined by fluorescence after reaction with fluorescamine with overall conditions and procedures similar to those of Fields, G. B., Van Wart, H. E., and Birkedal-Hansen, H. (1987) J. Biol. CHem. 262, 6221.

In the following table $K_i$ values are micromolar and are calculated from the measured percent inhibition using the $K_m$ value, and assuming competitive inhibition. HFS is Human Fibroblast Stromelysin. HFC is Human Fibroblast Collagenase. HNC is Human Neutrophil Collagenase.

| Compound of Example | HFS | HFC | HNC |
| --- | --- | --- | --- |
| 2 | 0.015 | 1.45 | <0.002 |
| 3 | 2.19 | 0.03 | 0.007 |
| 4 | 14.56 | 3.35 | 0.270 |
| 5 | 0.378 | 5.10 | <0.002 |
| 6 | 1.50 | 0.15 | 0.020 |
| 8 | 0.057 | 1.4 | 0.005 |
| 9 | 5.00 | 0.027 | 0.017 |
| 10 | 0.044 | 2.27 | 0.21 |
| 11 | 0.109 | 0.92 | 0.004 |
| 12 | 0.70 | 1.6 | 0.120 |
| 13 | 0.028 | 0.008 | — |
| 14 | 0.014 | 0.026 | — |
| 15 | 0.026 | 0.035 | 0.016 |
| 16 | 0.017 | 0.014 | — |
| 17 | 0.009 | 0.021 | — |
| 19 | 0.22 | 1.8 | — |

Although this invention has been described with respect to specific modification, the details thereof are not to be construed as limitations, for it will be apparent that various equivalents, changes and modifications may be restored and modification may be resorted to without departing from the spirit and scope thereof and it is understood that such equivalent embodiments are intended to be included therein.

We claim:

1. A compound of the formula

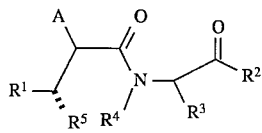

wherein

A is $A^1$-$A^2$-$A^3$ $A^1$ is $C_{1-10}$ alkyl, $C_{2-10}$ alkene, or $C_{2-10}$ alkyne having $C_{1-5}$ in the backbone;

$A^2$ is X - Y - Z; wherein

X is a chemical bond, —O—, or —S—;

Y is —$CHR^9$;

Z is —O—, —NH—, or —S—;

$A^3$ is
  hydrogen,
  substituted $C_{1-6}$ alkyl,
  aryl selected from the group consisting of phenyl and naphthyl,
  substituted phenyl or naphthyl,
  heteroaryl, wherein said aryl is phenyl or naphthyl,
  substituted heteroaryl wherein said aryl is phenyl or naphthyl,
  aryl $C_{1-6}$ alkyl, wherein said aryl is phenyl or naphthyl,
  substituted aryl $C_{1-6}$ alkyl, wherein said aryl is phenyl or naphthyl,
  heteroaryl $C_{1-6}$ alkyl, wherein said aryl is phenyl or naphthyl,
  substituted heteroaryl $C_{1-6}$ alkyl, wherein said aryl is phenyl or naphthyl, with the proviso that
  (a) at least of X, Y and Z must contain a heteroatom;
  (b) when Y is —$CH_2$— then only one of X and Z can be a heteroatom;
  (c) when $A^1$ is alkyl, X is a chemical bond, Y is $CHR^9$ and Z is —O—or —S—, then $A^3$ cannot be $C_{1-6}$ alkyl;

$R^1$ is
  HN(OH)CO—;

$R^2$ is
  $NR^{10}R^6$ wherein $R^6$ is
  hydrogen,
  $C_{6-12}$ aryl, or
  $(CH_2)_n R^7$,
  wherein $R^7$ is
    hydrogen
    phenyl,
    substituted phenyl,
    hydroxy,
    $C_{1-6}$ alkoxy,
    $C_{2-7}$ acyloxy,
    $C_{1-6}$ alkylthio,
    phenylthio,
    sulfoxide of a thio,
    sulfone of a thio,
    ($C_{1-6}$ alkyl) carbonyl,
    ($C_{1-6}$ alkoxy) carbonyl,
    ($C_{1-6}$ alkyl)aminocarbonyl,
    arylaminocarbonyl, wherein aryl is phenyl or naphthyl,
    amino,
    substituted acyclic amino,
    N-oxide of an amine, or
    $C_{2-7}$ acylamino, and
    n is 2 to 6; or $R^3$ and $R^6$ taken together are a group of the formula —$(CH_2)_m$— where m is from 5 to 12, optionally interrupted by a $NR^8$ group wherein $R^8$ is selected from
  hydrogen
  $C_{1-6}$ alkyl,
  $C_{1-6}$ alkylcarbonyl,
  $C_{1-6}$ alkoxycarbonyl,
  aryl,
  aralkyl, or
  aralkyloxycarbonyl,
  in each of which the aryl moiety is phenyl or naphthyl and is optionally substituted;

$R^3$ is a characterizing group of an alpha amino acid
  ethyl, butyl, pentyl or hexyl,
  $C_{3-10}$ cycloalkyl,
  aryl methylene,
  substituted aryl methylene,
  $C_{3-10}$ cycloalkyl methylene,
  phenyl,
  naphthyl,
  substituted phenyl,
  substituted naphthyl,
  fused bicycloaryl methylene,
  fused substituted bicycloaryl methylene,
  conjugated bicycloaryl methylene, or
  conjugated substituted bicycloaryl ethylene;

$R^4$ is $C_{1-4}$ alkyl;

$R^5$ is
  hydrogen phenyl,
substituted phenyl,
amino,
hydroxy,
mercapto,
$C_{1-4}$ alkoxy,
$C_{1-6}$ alkylamino,
$C_{1-6}$ alkylthio,
$C_{1-6}$ alkyl or $C_{2-6}$ alkenyl,
  optionally substituted by
    alkyl,
    phenyl,
    substituted phenyl,
    amino,
    acylated amino,
    protected amino,
    hydroxy,
    protected hydroxy,
    mercapto,
    protected mercapto,
    carboxy,
    protected carboxy, or
    amidated carboxy;
$R^9$ is hydrogen or $C_{1-4}$ alkyl,
$R^{10}$ is $C_{1-4}$ alkyl;
and the salts, solvates and hydrates thereof.

2. A pharmaceutical composition comprising an effective amount of a compound of claim 1.

3. A compound of the structure

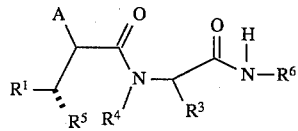

wherein

A is $A^1$–$A^2$–$A^3$
wherein
$A^1$ is $(CH_2)_n$, and n is 3–5,
$A^2$ is X - Y - Z,
wherein
X is a chemical bond, —NH—;
Y is —(C=O)—, —$CH_2$—, —($CHCH_3$)—,
Z is —O— or —NH—, and
$A^3$ is hydrogen, methyl, ethyl, propyl, butyl, pentyl, phenyl, methylphenyl, chlorophenyl, methoxyphenyl, phenylmethylene, methoxyphenylmethylene, methylphenylmethylene, or phenylethylene,
$R^1$ is HN(OH)CO—,
$R^3$ is
  tertiaryl butyl,
  phenylmethylene,
  cyclohexyl methylene, or
  3,5 dimethyl phenylmethylene;
$R^4$ is independently hydrogen or methyl;
$R^5$ is
  hydrogen, methyl, 2-methylpropropyl, 1,3-dihydro-1,3-dioxo-2H-isoindol-2-yl or tertiary butyl; and
$R^6$ is
  methyl, 2-pyridylethylene, phenylethylene or 4 sulfamoyl phenylethylene.

4. A compound of claim 3
wherein A is

—$(CH_2)_4$—O—H,
—$(CH_2)_3$—C=O—O—H,
—$(CH_2)_3$—C=O—NH—$(CH_2)_2CH_3$,
—$(CH_2)_3$—C=O—NH—$(CH_2)_2$-phenyl,
—$(CH_2)_3$—$CH(CH_3)$—O—H,
—$(CH_2)_4$—NH—C=O—$(CH_2)_2CH_3$,
—$(CH_2)_4$—O—phenyl,
—$(CH_2)_4$—O—(4-chlorophenyl),
—$(CH_2)_4$—O—(3-methylphenyl),
—$(CH_2)_4$—O—(4-methoxyphenyl),
—$(CH_2)_4$—O—(4-methylphenyl),
—$(CH_2)_5$—O—phenyl,
—$(CH_2)_4$—O—$CH_2$-phenyl,
—$(CH_2)_5$—O—$CH_2$—(4-methylphenyl), or
—$(CH_2)_3$—O—$CH_2$—(4-methylphenyl).

5. A pharmaceutical composition comprising an effective amount of a compound of claim 4.

6. A method of promoting an antiarthritic effect in a mammal in need thereof comprising administering thereto a matrix metalloproteinase inhibitory effective amount of a compound of claim 4.

7. A compound of claim 4 being:
a) N-[(2R)-2-[2'-(Hydroxyamino)-2'-(oxo)ethyl]-5-(carboxy)pentanoyl]-L-phenylalanine N-methylamide;

b) N-[(2R)-2-[2'-(Hydroxyamino)-2'-(oxo)ethyl]-6-(phenylmethoxy)hexanoyl]-L-phenylalanine N-methylamide;

c) N-[(2R)-2-[2'-(Hydroxyamino)-2'-(oxo)ethyl]-6-(propylamino)-6-(oxo)hexanoyl]-L-phenylalanine N-methylamide;

d) [(2R)-2-[2'-(Hydroxyamino)-2'-(oxo)ethyl]-(6RS)-6-(hydroxy)heptanoyl]-L-phenylalanine N-methylamide;

e) (2S)-N-2-[(2'R)-2'-[2''(Hydroxyamino-2''-(oxo)ethyl]-6'-(hydroxy)hexanoyl]amino-3,3-dimethylbutanoic acid N-methylamide;

f) (2S)-N-2-[(2'R)-2'-[2''-(Hydroxyamino)-2''-(oxo)ethyl]-6'-(phenylmethoxy)hexanoyl]amino-3,3-dimethylbutanoic acid N-methylamide;

g) N-[(2'R)-2-[2'-(Hydroxyamino)-2'-(oxo)ethyl]-6-(4'-oxobutylamino)hexanoyl]-L-phenylalanine N-methylamide;

h) 2(S)-N-2-[(2'R)-2'-[2''-(Hydroxyamino)-2''-(oxo)ethyl]-6'-(oxo)-6'-(propylamino)hexanoyl]amino-3,3-dimethylbutanoic acid N-methylamide;

i) N-[(2R)-2-[(1'S)-1'-(Methyl)-2'-(hydroxyamino)-2'-(oxo)-ethyl]-6-(phenylmethoxy)hexanoyl]-L-phenylalanine N-methylamide;

j) N-[(2R)-2-[(1'S)-1'-(Methyl)-2'-(hydroxyamino)-2'-(oxo)-ethyl]-6-(oxo)-6-(propylamino)hexanoyl]-L-phenylalanine N-methylamide;

k) N-[(2R)-2-[2'-(Hydroxyamino)-2'-(oxo)ethyl]-6-(oxo)-6-(propylamino)hexanoyl]-L-phenylalanine N-2-phenylethylamide;

l) (2S)-N-2-[(2'R)-2'-[(1''S)-1''-(Methyl)-2''-(hydroxyamino)-2''-(oxo)ethyl]-6-(phenylmethoxy(hexanoyl]amino-3,3-dimethylbutanoic acid N-2-phenylethylamide;

m) (2S)-N-2-[(2'R)-2'-[(1''S)-1''-(Methyl)-2''-(hydroxyamino)-2''-(oxo)ethyl]-6'-(oxo)-6'-(propylamino)hexanoyl]amino-3,3-dimethylbutanoic acid N-2phenylethylamide;

n) (2S)-N-2-[(2'R)-2'-[(1''S)-1''-(Methyl)-2''-(hydroxyamino)-2''-(oxo)ethyl]-6'-(oxo)-6'-(propylamino)hexanoyl]amino-3,3-dimethylbutanoic acid N-2-(4'-sulfamoyl)phenylethylamide;

o) (2S)-N-[(2'R)-2'-[2"-(Hydroxyamino)-2"-(oxo)ethyl]-6'-(phenylmethoxy)hexanoyl]amino-3-cyclohexylpropionic acid N-2-(4'-sulfamoyl)phenylethylamide;

p) N-[(2R)-2-[2'-(Hydroxyamino)-2'-(oxo)ethyl]-6'-(phenylmethoxy)hexanoyl]-L-(3,5-dimethyl)phenylalanine N-2-(4'-sulfamoyl)phenylethylamide;

q) (2S)-N-2'-[(2'R)-2'-[2"-(hydroxyamino)-2"-(oxo)ethyl]-6'-[(4-methoxy)phenoxy]hexanoyl]amino-3,3-dimethylbutanoic acid N-2-(4'-sulfamoyl)phenylethylamide;

r) (2S)-N-2'-[(2'R)-2'-[2"-(hydroxyamino)-2"-(oxo)ethyl]-6'-[(4-methyl)phenoxyl]hexanoyl]amino-3,3-dimethylbutanoic acid N-2-(4'-sulfamoyl)phenylethylamide;

s) (2S)-N-2'-[(2'R)-2'-[2"-(Hydroxyamino)-2"-(oxo)ethyl]-6'-[(1-oxo)butylamino]hexanoyl]amino-3-cyclohexylpropionic acid N-2-(4'-sulfamoyl)phenylethylamide;

t) (2S)-N-2-[(2'R)-2'-[(1"S)-1"-(Methyl)-2"-)hydroxyamino)-2"(oxo)ethyl]-6-(phenylmethoxy)hexanoyl]amino-3,3-dimethylbutanoic acid N-methylamide;

u) (2S)-N-2-[(2'R)-2'-[(1"S)-1"-(2-Methylpropyl)-2"-(hydroxyamino)-2"-(oxo)ethyl]-6-(phenylmethoxy)hexanoyl]amino-3,3-dimethylbutanoic acid N-methylamide;

v) N-[(2R)-2-[2'-(Hydroxyamino)-2'-(oxo)ethyl]-6-(phenoxy)-hexanoyl]-L-phenylalanine N-methylamide;

w) N-[(2R)-2-[2'-(Hydroxyamino)-2'-(oxo)ethyl]-7-(phenoxy)-heptanoyl]-L-phenylalanine N-methylamide;

x) (2S)-N-2'-[(2'R)-2'-[2"-(Hydroxyamino)-2"-(oxo)ethyl]-6'-(phenylmethoxy)hexanoyl]amino-3,3-dimethylbutanoic acid N-2-phenylethylamide;

y) (2S)-N-2'-[(2'R)-2'-[2"-Hydroxyamino)-2"-(oxo)ethyl]-6'-(phenylmethoxy)hexanoyl]amino-3,3-dimethylbutanoic acid N-2-(4'-sulfamoyl)phenylethylamide;

z) N-[(2R)-2-[2'-(Hydroxyamino)-2'-(oxo)ethyl]-5-(phenylmethoxy)pentanoyl]-L-phenylalanine N-methylamide;

aa) N-[(2R)-2-[2'-(Hydroxyamino)-2'-(oxo)ethyl]-7-(phenylmethoxy)heptanoyl]-L-phenylalanine N-methylamide;

ab) N[(2R)-2-[2'-(Hydroxyamino)-2'-(oxo)ethyl]-6-(phenyloxy)hexanoyl]-L-phenylalanine N-methylamide;

ac) N-[(2R)-2-[2'-(Hydroxyamino)-2'-(oxo)ethyl]-7-[(phenyloxy)heptanoyl]-L-phenylalanine N-methylamide;

ad) (2S)-N-2'-[(2'R)-2'-[2"-(Hydroxyamino)-2"-(oxo)ethyl]-6'-[(2-phenethylamino)-6'-(oxo)hexanoyl]amino-3,3-dimethylbutanoic acid N-methylamide;

ae) (2S)-N-2'-[(2'R)-2'-[2"-(Hydroxyamino)-2"-(oxo)ethyl]-6'-[(4-methylphenoxy)hexanoyl]amino-3,3-dimethylbutanoic acid N-methylamide;

af) (2S)-N-2'[(2'R)-2'-[2"-(Hydroxyamino)-2"-(oxo)ethyl]-6'-[(4-chlorophenoxy)hexanoyl]amino-3,3-dimethylbutanoic acid N-methylamide;

ag) (2S)-N-2'-[(2'R)-2'-[2"-(Hydroxyamino)-2"-(oxo)ethyl]-6'-[(3-methylphenoxy)hexanoyl]amino-3,3-dimethylbutanoic acid N-methylamide; and ah) (2S)-N-2'-[(2'R)-2'-(carboxymethyl-6'-(3-methylphenoxy)hexanoyl]amino-3,3-dimethylbutanoic acid N-methylamide.

8. A method of promoting an antiarthritic effect in a mammal in need thereof comprising administering thereto a matrix metalloproteinase inhibitory effective amount of a compound of claim 7.

9. A pharmaceutical composition comprising an effective amount of a compound of claim 7.

10. A pharmaceutical composition comprising an effective amount of a compound of claim 3.

11. A method of promoting an antiarthritic effect in a mammal in need thereof comprising administering thereto a matrix metalloproteinase inhibitory effective amount of a compound of claim 3.

12. The compound N-[(2R)-2-[2'-hydroxyamino)-2'-(oxo)ethyl]-6-(hydroxy)hexanoyl]-L-phenyl-alanine N-methylamide.

13. A pharmaceutical composition comprising an effective amount of the compound of claim 12.

14. A method of promoting an antiarthritic effect in a mammal in need thereof comprising administering thereto a matrix metalloproteinase inhibitory effective amount of the compound of claim 12.

15. A method of promoting an antiarthritic effect in a mammal in need thereof comprising administering thereto a matrix metalloproteinase inhibitory effective amount of a compound of the formula:

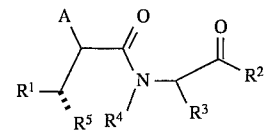

wherein

A is $A^1$–$A^2$–$A^3$ $A^1$ is $C_{1-10}$ alkyl, $C_{2-10}$ alkene, or $C_{2-10}$ alkyne having $C_{1-5}$ in the backbone;

$A^2$ is X - Y- Z; wherein

X is a chemical bond, —O—, or —S—;

Y is —$CHR^9$;

Z is —O—, —NH—, or —S—;

$A^3$ is
  hydrogen,
  substituted $C_{1-6}$ alkyl,
  aryl selected from the group consisting of phenyl and naphthyl,
  substituted phenyl or naphthyl,
  heteroaryl, wherein said aryl is phenyl or naphthyl,
  substituted heteroaryl wherein said aryl is phenyl or naphthyl,
  aryl $C_{1-6}$ alkyl, wherein said aryl is phenyl or naphthyl,
  substituted aryl $C_{1-6}$ alkyl, wherein said aryl is phenyl or naphthyl,
  heteroaryl $C_{14\ 6}$ alkyl, wherein said aryl is phenyl or naphthyl,
  substituted heteroaryl $C_{1-6}$ alkyl, wherein said aryl is phenyl or naphthyl, with the proviso that
  (a) at least of X, Y and Z must contain a heteroatom;
  (b) when Y is —$CH_2$— then only one of X and Y can be a heteroatom;
  (c) when $A^1$ is alkyl, X is a chemical bond, Y is $CHR^9$ and Z is —O— or —S—, then $A^3$ cannot be $C_{1-6}$ alkyl;

$R^1$ is
  HN(OH)CO—;

$R^2$ is
  $NR^{10}R^6$ wherein $R^6$ is
  hydrogen, $C_{6-12}$ aryl, or
$(CH_2)_nR^7$,
wherein $R^7$ is
  hydrogen,
  phenyl,
  substituted phenyl,
  hydroxy,
  $C_{1-6}$ alkoxy,
  $C_{2-7}$ acyloxy,
  $C_{1-6}$ alkylthio,
  phenylthio,
  sulfoxide of a thio,
  sulfone of a thio,
  ($C_{1-6}$ alkyl) carbonyl,
  ($C_{1-6}$ alkoxy) carbonyl,
  ($C_{1-6}$ alkyl)aminocarbonyl,
  arylaminocarbonyl, wherein aryl is phenyl or naphthyl,
  amino,
  substituted acyclic amino,
  N-oxide of an amine, or
  $C_{2-7}$ acylamino, and
  n is 2 to 6 : or
$R^3$ and $R^6$ taken together are a group of the formula
—($CH_2$)— where m is from 5 to 12, optionally interrupted by a $NR^8$ group
where $R^8$ is selected from
  hydrogen
  $C_{1-6}$ alkyl,
  $C_{1-6}$ alkylcarbonyl,
  $C_{1-6}$ alkoxycarbonyl,
  aryl,
  aralkyl, or
  aralkyloxycarbonyl,
  in each of which the aryl moiety is phenyl or naphthyl and is optionally substituted;
$R^3$ is a characterizing group of an alpha amino acid
  ethyl, butyl, pentyl or hexyl,
  $C_{3-10}$ cycloalkyl,
  aryl methylene,
  substituted aryl methylene,
  $C_{3-10}$ cycloalkyl methylene,
  phenyl,
  naphthyl,
  substituted phenyl,
  substituted naphthyl,
  fused bicycloaryl methylene,
  fused substituted bicycloaryl methylene,
  conjugated bicycloaryl methylene, or
  conjugated substituted bicycloaryl ethylene;
$R^4$ is $C_{1-4}$ alkyl;
$R^5$ is
  hydrogen,
  phenyl,
  substituted phenyl,
  amino,
  hydroxy,
  mercapto,
  $C_{1-4}$ alkoxy,
  $C_{1-6}$ alkylamino,
  $C_{1-6}$ alkylthio,
  $C_{1-6}$ alkyl or $C_{2-6}$ alkenyl,
    optionally substituted by
      alkyl,
      phenyl,
      substituted phenyl,
      amino,
      acylated amino,
      protected amino,
      hydroxy,
      protected hydroxy,
      mercapto,
      protected mercapto,
      carboxy,
  protected carboxy, or
  amidated carboxy;
$R^9$ is hydrogen or $C_{1-4}$ alkyl;
$R^{10}$ is $C_{1-4}$ alkyl;
and the salts, solvates and hydrates thereof.

* * * * *